US008664186B2

(12) United States Patent
Aigle et al.

(10) Patent No.: US 8,664,186 B2
(45) Date of Patent: Mar. 4, 2014

(54) STAMBOMYCIN AND DERIVATIVES, THEIR PRODUCTION AND THEIR USES AS DRUGS

(75) Inventors: Bertrand Aigle, Laxou (FR); Gregory Challis, Leics (GB); Luisa Laureti, Issy les Moulineaux (FR); Lijiang Song, Conventry (GB); Pierre Leblond, Flavigny-sur-Moselle (FR)

(73) Assignees: Universite de Lorraine, Nancy (FR); University of Warwick, Coventry (GB); Institut National de la Recherche Agronomique, Paris (FR)

( * ) Notice: Subject to any disclaimer, the term of this patent is extended or adjusted under 35 U.S.C. 154(b) by 29 days.

(21) Appl. No.: 13/378,954

(22) PCT Filed: Jul. 23, 2010

(86) PCT No.: PCT/EP2010/060707
§ 371 (c)(1),
(2), (4) Date: Feb. 21, 2012

(87) PCT Pub. No.: WO2011/009938
PCT Pub. Date: Jan. 27, 2011

(65) Prior Publication Data
US 2012/0142622 A1 Jun. 7, 2012

(30) Foreign Application Priority Data
Jul. 24, 2009 (EP) .................................... 09290587

(51) Int. Cl.
A61K 31/70 (2006.01)
C07H 17/08 (2006.01)
C12P 19/62 (2006.01)
C12N 1/20 (2006.01)

(52) U.S. Cl.
USPC .............. 514/31; 536/6.5; 435/76; 435/253.5

(58) Field of Classification Search
USPC ......................................................... 536/6.5
See application file for complete search history.

(56) References Cited

FOREIGN PATENT DOCUMENTS

| EP | 0 791 655 A2 | 8/1997 |
| WO | 00/00618 A2 | 1/2000 |
| WO | 2006/045063 A2 | 4/2006 |

OTHER PUBLICATIONS

Challis Gregory L: "Mining microbial genomes for new natural products and biosynthetic pathways", Microbiology (Reading), vol. 154, No. Part 6, Jun. 2008, pp. 1555-1569, XP002585719, ISSN: 1350-0872, in the application the whole document in particular p. 154, Left-hand column, second paragraph, in European Search Report and ISR.

Yadav Gitanjali et al.: "SEARCHPKS: A program for detection and analysis of polyketide synthase domains", Nucleic Acids Research, Oxford University Press, GB LNKD- D0I:10.1093/NAR/GKG607, vol. 31, No. 13, Jul. 1, 2003, pp. 3654-3658, XP002517616, ISSN: 1362-4962, in the application abstract, in European Search Report and ISR.

Karray Fatma et al.: "Organization of the biosynthetic gene cluster for the macrolide antibiotic spiramycin in *Streptomyces ambofaciens*", Microbiology, Society for General 10.099/MIC.0.2007/009746-0, vol. 153, no, Part 12, Dec. 1, 2007, pp. 4111-4122, XP002481781, ISSN: 1350-0872 in the application the whole document "Regulatory genes"; p. 4119, left-hand column, paragraph third, in European Search Report and ISR.

Chou Let Frederic et al.: "Intraspecific variability of the terminal inverted repeats of the linear chromosome of *Streptomyces ambofaciens*", Journal of Bacteriology, vol. 188, No. 18, Sep. 2006, pp. 6599-6610, XP002585720, ISSN: 0021-9193, in the application, abstract p. 6601, left-hand column, paragraph, in European Search Report and ISR.

Barona-Gomez Francisco et al.: "Multiple biosynthetic and uptake systems mediate siderophore-dependent iron acquisition in *Streptomyces coelicolor* A3(2) and *Streptomyces ambofaciens* ATCC 23877", Microbiology (Reading), vol. 152, No. Part 11, Nov. 2006, pp. 3355-3366, XP002585721, I SSN: 1350-0872 in the application abstract, in European Search Report and ISR.

European Search Report, dated Jun. 7, 2010, from corresponding European application.

International Search Report, dated Mar. 22, 2011, from corresponding PCT application.

*Primary Examiner* — Elli Peselev
(74) *Attorney, Agent, or Firm* — Young & Thompson

(57) ABSTRACT

The present invention relates to Stambomycin compounds, their derivatives and their pharmaceutically acceptable salt thereof.

12 Claims, 20 Drawing Sheets

| | | | | |
|---|---|---|---|---|
| KR1 | PHDTVLITGGTGALGARVARHLVCAHGVAGLVLLS-47-VVHTAGVLDGLLTSLTPE-26-FVLFSSVAASFGTAGQASYMAANAFLD | B1 |
| KR2 | -DGTVLVTGGTGALGAQVAR-LLAARGHNRLLIVS-51-VVHAAGVLDEGVIDGLTPE-26-FVLFSSFTGAVGTAGQANYLAANAHLD | B1 |
| KR3 | --GTVLVTGGTGALGAHTARLLARR-GVPHLVLVG-51-VVHAAGTVDDGVIGSLTPG-26-FVLYTSFAGWVGNLQQAYLAANAALD | B1 |
|

| | | | | | |
|---|---|---|---|---|---|
| AT1 | AMIFSGQGS-53-VVQPA-22-VAGHSQGEI-18-VALRS-70-PVDYASHSAHVE-45-LRSTVEFSA | | | | |
| AT2 | GFLFTGQGS-50-YAQAG-22-LVGHSIGNL-18-VSARG-66-AVSHAFHSRLME-40-IREPVRFAD | | | | |
| AT3 | GFLFTGQGS-50-YAQAG-22-LVGHSVGEI-18-VSARG-66-AVSHAFHSRLME-40-VREPVRFAD | | | | |
| AT4 | ALLFSGQGS-50-YAQAG-22-LVGHSIGEL-18-VSARG-66-AVSHAFHSRLME-40-VREPVRFAD | | | | |
| AT5 | AFLFSGQGA-50-YTQPA-22-LVGHSIGEL-18-VSARA-66-AVSHAFHSRLME-40-IVAPVRFAD | | | | |
| AT6 | VFVFPGQGS-52-VVQPV-22-VVGHSQGEI-18-VALRS-71-PVDYASHSVQVE-45-LRSTVRFEE | | | | |
| AT7 | GFLFTGQGA-51-WTQAG-22-LLIGHSIGEV-18-VEARG-68-TVSHAFHSALME-46-VRQAVRFAD | | | | |
| AT8 | VFVFPGQGS-52-VVQPV-22-VVGHSQGEI-18-VALRS-71-PVDYASHSVQVE-45-LRSTVRFEE | | | | |
| AT9 | AFLFTGQGA-50-WTQAG-22-LIIGHSIGEI-18-VAARG-68-TVSHAFHSALME-41-VRETVRFAD | | | | |
| AT10 | AFLFTGQGA-50-WAQAG-22-LVGHSVGEI-18-VAQRG-68-TVSHAFHSVLME-41-VRETVRFGD | | | | |
| AT11 | AFLFTGQGA-50-WAQAG-22-LIIGHSIGEL-18-VAARG-68-TVSHAFHSVLME-46-VREAVRFAD | | | | |
| AT12 | ALLFSGQGS-50-YAQAG-22-LVGHSIGNI-18-VSARG-66-AVSHAFHSRLME-40-VREPVRFAD | | | | |
| AT13 | AFVLPGQGS-53-VIQPV-22-VVGHSQGEI-18-VTHRS-71-RIKGAFHSAVVE-45-MRQTVQFAP | | | | |
| AT14 | AFVFPGQGG-53-VTPVV-22-VIGHSVGEL-18-VALRG-71-RVDFSSHCAQVE-45-LVTPVD_DR | | | | |
| AT15 | AFLFSGQGA-50-YAQVE-22-LVGHSVGEI-18-VAARG-66-AVSHAFHSRLME-40-VREPVRFAD | | | | |
| AT16 | AFLFSGQGS-50-YAQAG-22-LIIGHSIGEL-18-VSARG-66-AVSHAFHSRLME-40-VREPVRFAD | | | | |
| AT17 | ALLFSGQGS-50-YAQAG-22-LVGHSVGEL-18-VSARG-66-AVSHAFHSRRMD-40-VREPVRFAD | | | | |
| AT18 | VFVFPGQGS-53-VVQPV-22-VVGHSQGEI-18-VALRA-71-PVDYASHCAQVE-45-LRNTVRFEE | | | | |
| AT19 | ALLFSGQGS-50-YAQAG-22-LVGHSIGEL-18-VALRG-71-PVDYASHSHLME-40-VREPVRFAD | | | | |
| AT20 | AFLFTGQGA-49-HTQPA-22-LAGHSIGEL-18-VAARG-66-AVSHAFHSHLME-42-VRSTVRFAG | | | | |
| AT21 | VFVFPGQGS-51-VVQPV-22-VVGHSQGEI-18-VALRA-71-PVDYASHCAQVE-45-LRNTVRFEE | | | | |
| AT22 | VFVFPGQGS-51-VVQPV-22-VVGHSQGEI-18-VALRA-71-PVDYASHCAQVE-45-LRNTVRFEE | | | | |
| AT23 | ALLFSGQGS-50-YAQAG-22-LVGHSIGEL-18-VSARG-66-AVSHAFHSRLME-40-VREPVRFAD | | | | |
| AT24 | VFVFPGQGS-51-VVQPV-22-VVGHSQGEI-18-VALRA-71-PVDYASHSAHVE-45-LRATVRFED | | | | |
| AT25 | AFVFSGQGA-51-WTQLG-22-LAGHSVGNV-18-VAARG-71-DVSHAFHSPRVD-45-IRATVRFAD | | | | |
| | Q | | GH[QMI]G | R | SH | V | methylmalonyl-CoA |
| | Q | | GH[LVIFAM]G | R | [FP]H | V | malonyl-CoA |

FIGURE 3

STAMBOMYCIN AND DERIVATIVES, THEIR PRODUCTION AND THEIR USES AS DRUGS

FIELD OF THE INVENTION

The present invention relates to stambomycin compounds and derivatives. The invention also relates to a process for producing stambomycin compounds. The invention also relates to the use of stambomycin compounds, in particular as drugs.

BACKGROUND OF THE INVENTION

In the invention, stambomycin compounds can also be named sambomycin compounds as mentioned in the priority document EP 09290587.6 of Jul. 24, 2009.

Since the discovery of the first antibiotic secreted by a *Streptomyces* by Selman Waksman in 1942, many antibiotics have been developed by the pharmaceutical industry to treat bacterial infections.

However, the large use of single or multiple antibiotherapies have enhanced the emergence of resistant bacterial strains, which have developed mechanisms to resist said antibiotics. To date, some bacteria, such as *Staphylococcus aureus*, are resistant to more than 4 different antibiotics.

So, there is a need to provide new antibiotics that can treat bacterial infections, in particular infections caused by multi-drug resistant bacterial strains.

Streptomycetes are Gram-positive, filamentous, soil-living bacteria that undergo a complex program of morphological differentiation. In addition to this singular multi-cellular morphogenesis, the members of the *Streptomyces* genus are well known for their ability to produce various compounds via secondary metabolism with important uses in medicine and in agriculture. Recent advances in the sequencing of *Streptomyces* genomes, and more generally those of actinomycetes, have highlighted the underestimated potential of these organisms to biosynthesise secondary metabolites. Indeed, the analysis of *Streptomyces coelicolor* revealed the presence of 22 gene clusters with deduced roles in the production of secondary metabolites whereas only half a dozen of them were identified before (Bentley et al., *Nature*, 2002, 417: 141-147; Challis and Hopwood, *Proc Natl Acad Sci USA*, 2003, 100 Suppl 2: 14555-14561). Similarly, analysis of the *Streptomyces avermitilis* genome sequence revealed 30 secondary metabolite gene clusters (Ikeda et al., *Nat Biotechnol*, 2003, 21: 526-531). More recently, the genome sequences of non-*Streptomyces* actinomycetes such as the biotechnologically important *Rhodococcus* sp. RHA1 (Mc Leod et al., *Proc Natl Acad Sci USA*, 2006, 103: 15582-15587.), the potent anticancer salinosporamide A producer *Salinispora tropica* (Udwary et al., *Proc Natl Acad Sci USA*, 2007, 104: 10376-10381) and the erythromycin-producing bacterium *Saccharopolyspora erythraea* (Oliynyk et al., *Nat Biotechnol*, 2007, 25: 447-453) identified, in total, more than 70 clusters for the biosynthesis of secondary metabolites. From these sequences, a genome mining approach allowed, for instance, to discover the tris-hydroxamate tetrapeptide siderophore coelichelin from *S. coelicolor* A3(2) (Lautru et al., *Nat Chem Biol*, 2005, 1: 265-269). In *S. ambofaciens* ATCC 23877, which was known to produce congocidine (Cosar et al., *C R Hebd Seances Acad Sci*, 1952, 234: 1498-1499) and spiramycin (Pinnert-Sindico, *Ann Inst Pasteur (Paris)*, 1954, 87: 702-707), the sequencing of the left (1,544 kb; accession number AM238663) and right (1,367 kb; AM238664) arms of the linear chromosome, has unveiled eleven novel secondary metabolite gene clusters (http://www.weblgm.scbiol.uhp-nancy.fr/ambofaciens/, Choulet et al., *Mol Biol Evol*, 2006, 23: 2361-2369).

Except for the des cluster identified in the core region of the chromosome that directs the biosynthesis of desferrioxamines B and E, only the cch coelichelin biosynthetic gene cluster (Barona-Gomez et al., *Microbiology*, 2006, 152: 3355-3366) and clusters presumed to be involved in the biosynthesis of carotenoids are found to be the same as clusters present in the phylogenetically close relative *S. coelicolor*, highlighting the powerful ability of Streptomycetes to produce distinct secondary metabolites.

The international application WO2000/000618 discloses processes and materials for preparing novel polyketides, particularly 12-, 14- and 16-membered ring macrolides, by recombinant biosynthesis, and the novel polyketides thus produced. The process according to the international application discloses the use of specific genes of a type I PKS gene cluster for producing said macrolides.

Challis 2008 Microbiology vol 154, Part 6, p: 1555-1559 discloses methods developed to characterize the metabolic products of cryptic biosynthetic gene clusters.

Yadav et al. 2003 Nucleic Acid Research vol 31 no 13, p: 3654-3658 disclose a software SEARCHPKS allowing detection and analysis of polyketide synthase domains in a polypeptide sequence. SEARCHPKS can also aid in identification of polyketide products made by PKS clusters found in newly sequenced genomes.

Karray et al. 2007 Microbiology, vol 153 Part 12, p: 4111-4122 disclose the organisation of the cluster of genes allowing the biosynthesis of spiramycin by *Streptomyces ambofaciens*.

The European application EP 0791655 discloses the characterization of a new polyketide gene cluster allowing the production of tylactone.

The international application WO 2006/045063 discloses the biosynthesis of novel polyketides by incorporating starter units that differ from the natural starter units used in the native production of polyketides.

SUMMARY OF THE INVENTION

One aim of the present invention is to provide new compounds having biological effects. Another aim of the invention is to provide a process that allows the production of said compounds.

Another aim of the invention is to provide compositions comprising said compounds and their use as drugs for the treatment of pathologies.

The invention relates to compounds having general formula (I)

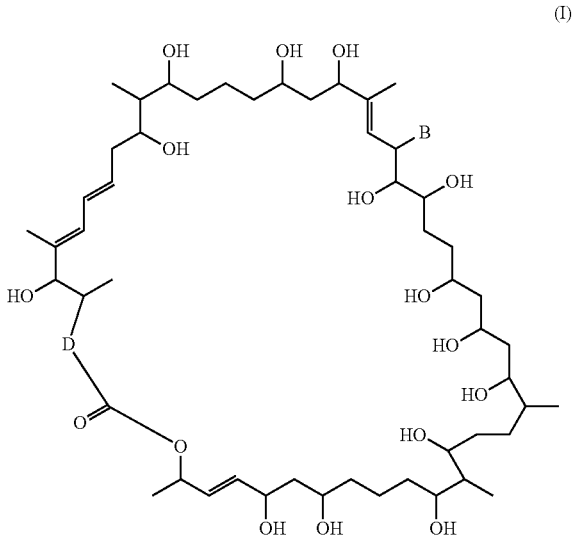

(I)

wherein

D represents:

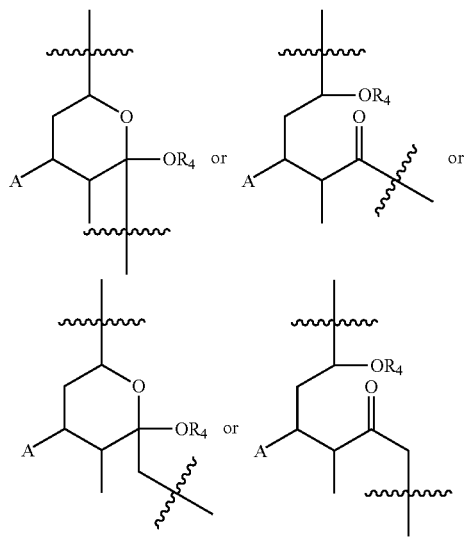

with A representing a sugar $C_5$-$C_6$, preferably a $C_5$-$C_6$ amino sugar, more preferably an amino sugar selected from the group comprising the amino sugars represented by the following formula:

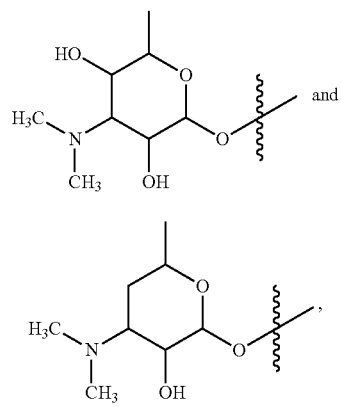

and with $R_4$ representing an hydrogen atom, or a linear or branched, substituted or not, saturated or not, $C_1$-$C_{12}$ alkyl, and B represents an hydrogen atom, or a linear or branched, substituted or not, saturated or not, $C_1$-$C_{12}$ alkyl, preferably a linear or branched, substituted or not, saturated or not, $C_5$-$C_{10}$ alkyl, more preferably a linear or branched, substituted or not, saturated or not, $C_6$-$C_8$ alkyl, and said compounds being in the form of a racemate, or anyone of their enantiomers or diastereomers, or anyone of the tautomers of said racemates and of said enantiomers and diastereomers, and their respective pharmaceutically acceptable salts.

The invention relates also to compounds having the following general formula (I-A)

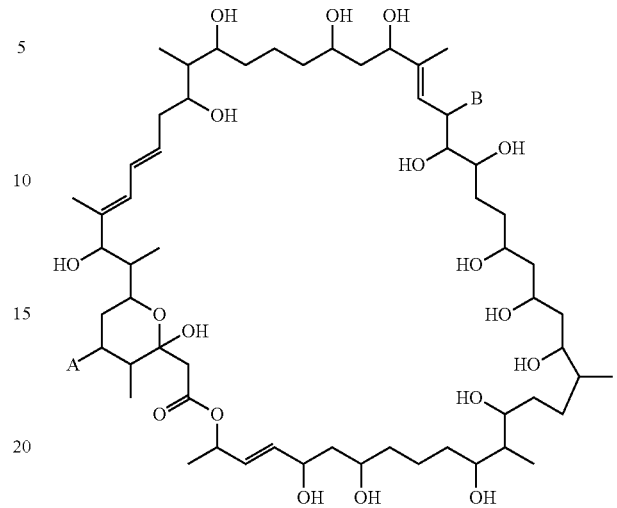

or having the following general formula (I-B)

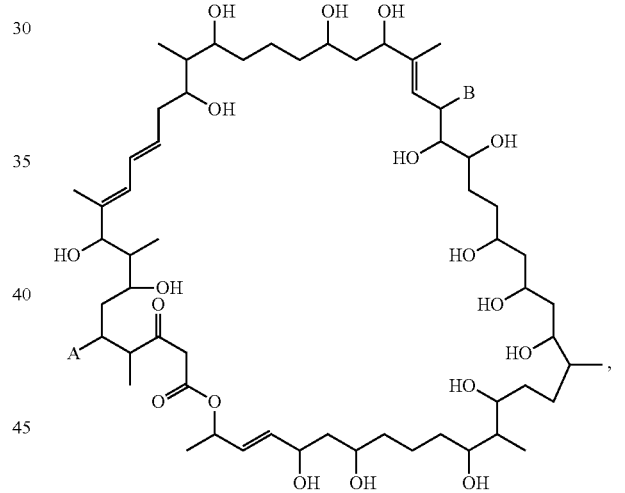

the tautomer of (I-A)

wherein

A represents a $C_5$-$C_6$ sugar, preferably a $C_5$-$C_6$ amino sugar, more preferably an amino sugar selected from the group comprising the amino sugars represented by the following formula:

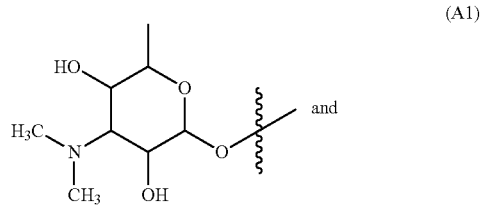

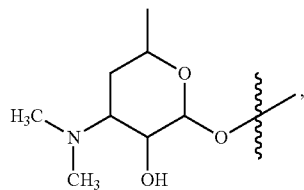

(A2)

and

B represents an hydrogen atom, or a linear or branched, substituted or not, saturated or not, $C_1$-$C_{12}$ alkyl, preferably a linear or branched, substituted or not, saturated or not, $C_5$-$C_{10}$ alkyl, more preferably a linear or branched, substituted or not, saturated or not, $C_6$-$C_8$ alkyl, said compounds being in the form of a racemate, or anyone of their enantiomers or diastereoisomers, or anyone of the tautomers of said racemates and of said enantiomers and diastereomers, and their respective pharmaceutically acceptable salts.

Hereafter, D will be only represented in the enol form. Both enol and keto form of D exist in an equilibrium state.

It is well known in the art that keto-enol tautomerism refers to a chemical equilibrium between a keto form (a ketone or an aldehyde) and an enol. The enol and keto forms are said to be tautomers of each other. The interconversion of the two forms involves the movement of a proton and the shifting of bonding electrons; hence, the isomerism qualifies as tautomerism.

DETAILED DESCRIPTION OF THE INVENTION

The invention is based on the characterization of the compounds having the formula (I). These compounds are novel.

In the invention, A group represents a $C_5$-$C_6$ sugar also called a $C_5$-$C_6$ monosaccharide, which has 5 carbon atoms or 6 carbon atoms.

The natural $C_5$ monosaccharides are also called pentoses and are represented by desoxyribose, ribose, arabinose, xylose, lyxose, ribulose and xylulose. The pentoses according to the invention may be under the form of furanose or pyranose which correspond to the cyclic forms of the pentoses. They are preferably in form of pyranoses. The natural $C_6$ monosaccharides are also called hexoses and are represented by allose, altrose, glucose, mannose, gulose, idose, galactose, talose, psicose, fructose, sorbose and tagatose. The hexoses according to the invention may be under the form of furanose or pyranose which correspond to the cyclic forms of the hexoses. They are preferably in form of pyranoses.

In the above mentioned furanoses or pyranoses, the anomeric center can be in a configuration α or β.

Preferably in the invention the $C_5$-$C_6$ sugars, or $C_5$-$C_6$ monosaccharides, are amino sugars.

Amino sugar refers, in the invention, to a monosaccharide wherein a hydroxyl group is substituted by an amino group. Amino sugars are also called aminoglycosides.

As for the monosaccharides from which they derive, amino sugars are preferably in a form of an aminopyranose (cyclic $C_6$ amino sugar) or in the form of an aminofuranose (cyclic $C_5$ amino sugar).

The amino sugar of the invention can be selected from the group comprising: galactosamine, glucosamine, N-acetyl glucosamine, mycaminose or desosamine. These examples are not limiting. Preferably, the amino sugar according to the invention is one of the amino sugars having the following formulae:

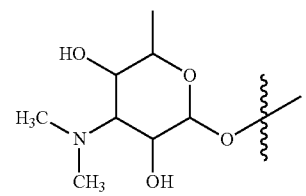

(A1)

which represents mycaminose, and

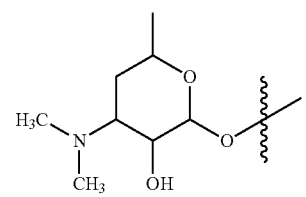

(A2)

which represents desosamine.

In the invention, B group can be a linear or branched $C_1$-$C_{12}$ alkyl, which means that B represents a carbon chain having 1, or 2, or 3, or 4, or 5, or 6, or 7, or 8, or 9, or 10, or 11, or 12 carbons. In other words, if said B group is a linear alkyl, B group can be a methyl, an ethyl, a propyl, a butyl, a pentyl, a hexyl, a heptyl, an octyl, a nonyl, a decyl, an undecyl and a dodecyl group.

An advantageous B group represents a linear or branched $C_5$-$C_{10}$ alkyl which means that B represents a carbon chain having 5, or 6, or 7, or 8, or 9, or 10 carbons.

Another advantageous B group represents a linear or branched $C_6$-$C_8$ alkyl which means that B represents a carbon chain having 6, or 7, or 8 carbons.

From the composition of the alkyl group, for instance 4 carbons, the skilled person can easily determine the corresponding branched alkyl group having 4 carbons: isobutyl, sec-butyl and tert-butyl.

The above mentioned alkyl groups can be unsaturated, which means that double or triple bounds can be present in the alkyl chain, with respect to the carbon valence.

The above mentioned alkyl groups, saturated or not, can be substituted, which means that some groups can be present such as hydroxyl groups, amino groups, acid groups or ester groups.

The compounds having the general formula (I) have many asymmetric carbons. Therefore, the compounds according to the invention can be in a form of any of their enantiomers or diastereoisomers. The compounds according to the invention can also be in a form of a racemic mixture, or racemate, of two enantiomers, each enantiomer of said racemic mixture being present in a ratio from 1:10 to 10:1, preferably from 1:5 to 5:1, more preferably in a ratio of 1:1.

Also the compounds according to the invention can be present in a form of the pharmaceutically acceptable salts known to a person skilled in the art, such as sodium salts, ammonium salts, calcium salts, magnesium salts, potassium salts, acetate salts, carbonate salts, citrate salts, chloride salts, sulphate salts, amino chlorhydate salts, borhydrate salts, phosphate salts, dihydrogenophosphate salts, succinate salts, citrate salts, tartrate salts, lactate salts, mandelate salts, methane sulfonate salts (mesylate) or p-toluene sulfonate salts (tosylate).

In one advantageous embodiment, the invention relates to compounds defined above, having the following general formula (II)

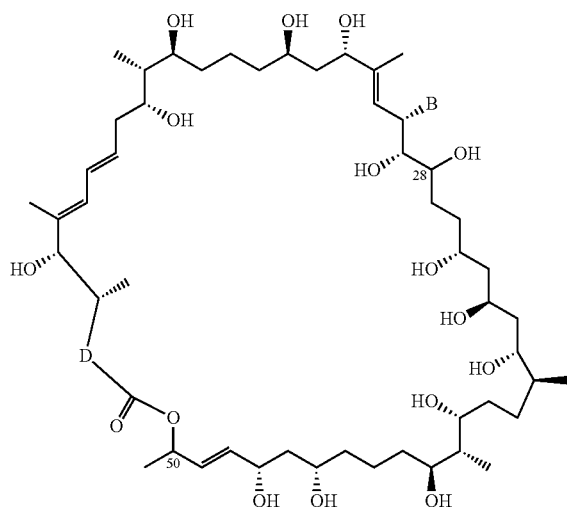

(II)

wherein

D represents

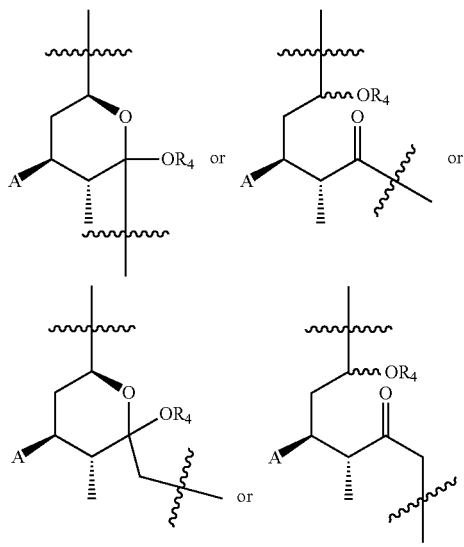

with A representing a sugar $C_5$-$C_6$, preferably a $C_5$-$C_6$ amino sugar, more preferably an amino sugar selected from the group comprising the amino sugars represented by the following formula:

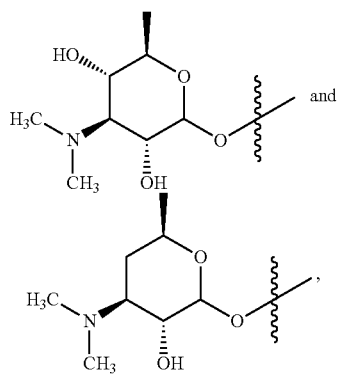

(A3)

(A4)

and with $R_4$ representing an hydrogen atom, or a linear or branched, substituted or not, saturated or not, $C_1$-$C_{12}$ alkyl, and B represents an hydrogen atom, or a linear or branched, substituted or not, saturated or not, $C_1$-$C_{12}$ alkyl, preferably a linear or branched, substituted or not, saturated or not, $C_5$-$C_{10}$ alkyl, more preferably a linear or branched, substituted or not, saturated or not, $C_6$-$C_8$ alkyl, and their respective pharmaceutically acceptable salts.

In one advantageous embodiment, the invention relates to compounds defined above, having the following general formula (II-A)

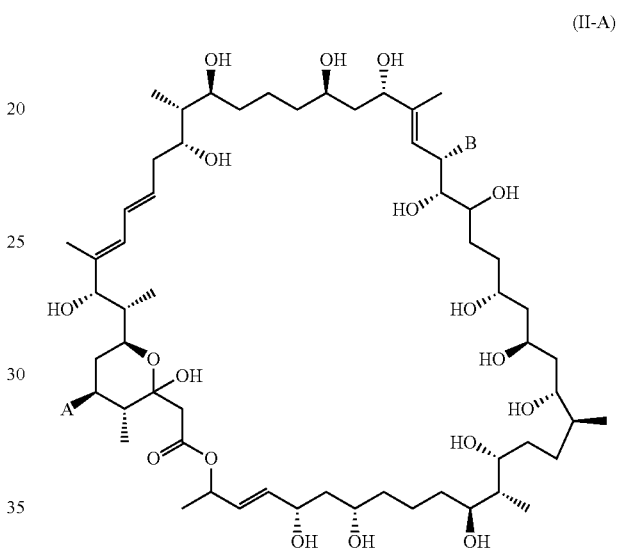

(II-A)

wherein

A represents a sugar $C_5$-$C_6$, preferably a $C_5$-$C_6$ amino sugar, more preferably an amino sugar selected from the group comprising the amino sugars represented by the following formula:

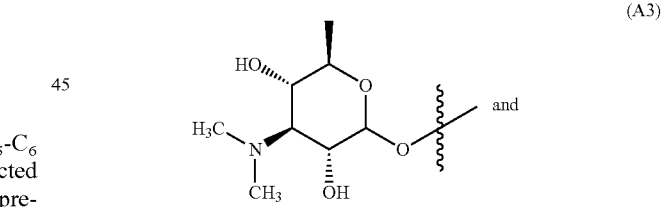

(A3)

(A4)

and

B represents an hydrogen atom, or a linear or branched, substituted or not, saturated or not, $C_1$-$C_{12}$ alkyl, preferably a linear or branched, substituted or not, saturated or not, $C_5$-$C_{10}$ alkyl, more preferably a linear or branched, substituted or not, saturated or not, $C_6$-$C_8$ alkyl, and their respective pharmaceutically acceptable salts.

Another advantageous embodiment of the invention relates to compounds previously defined and characterised in that B represents:

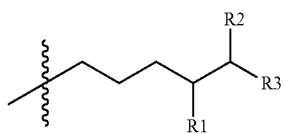

wherein R1, R2 and R3, independently from each other, represent:

an hydrogen atom, or
a linear or branched, substituted or not, saturated or not, $C_1$-$C_{12}$ alkyl, preferably a methyl group.

In another preferred embodiment, the invention relates to compounds defined above, said compounds being selected from the group comprising:

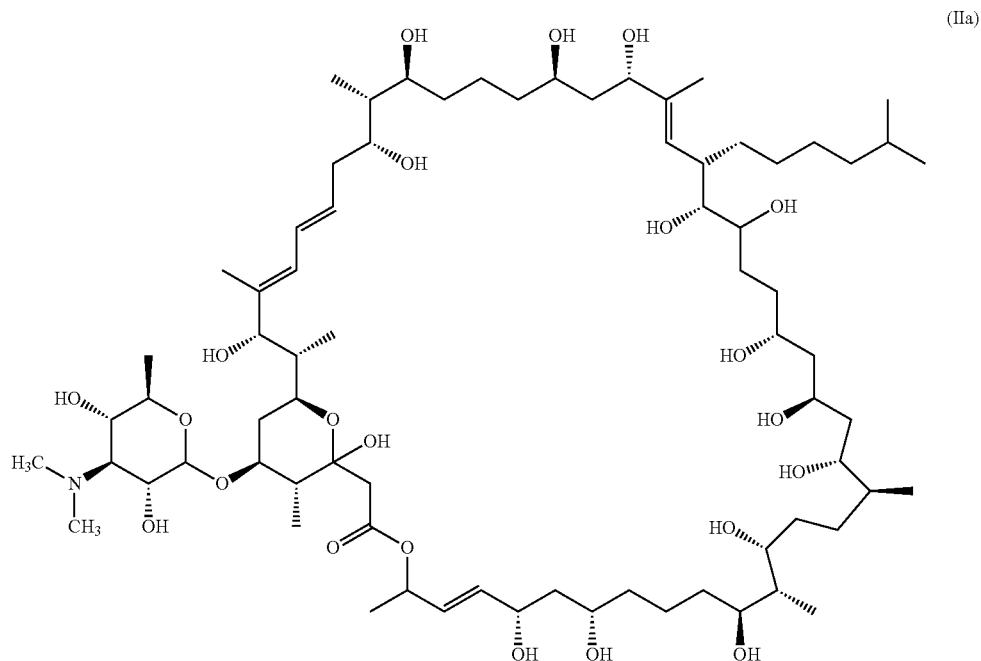
(IIa)

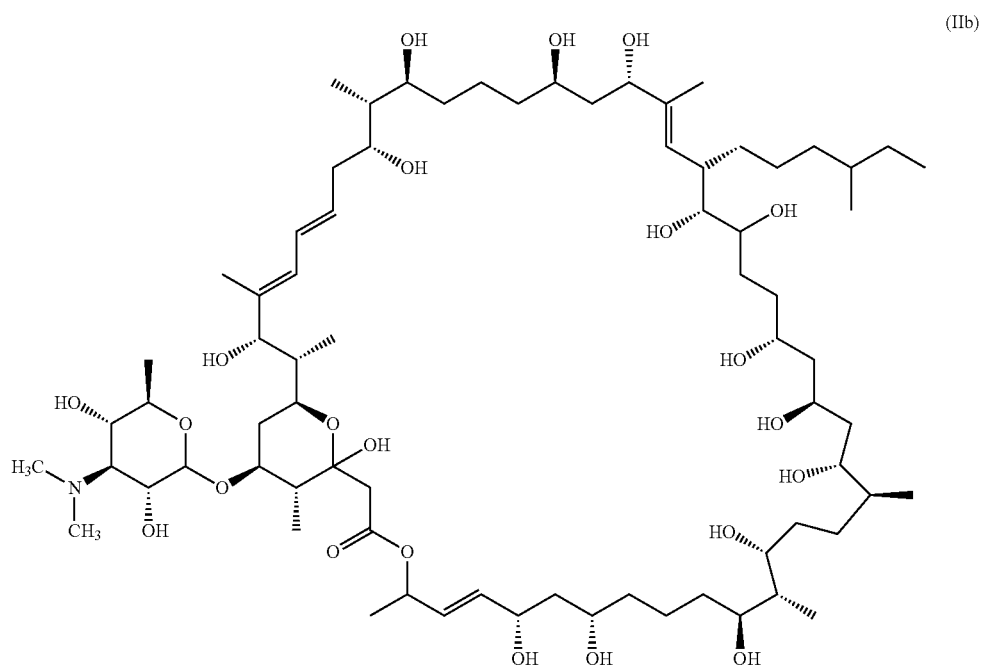
(IIb)

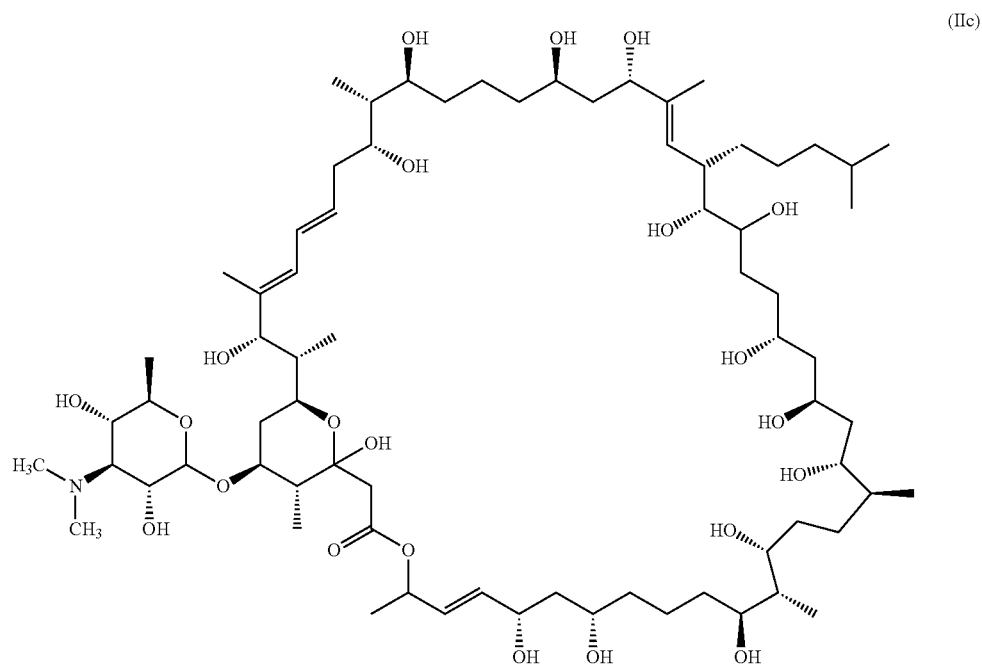
(IIc)
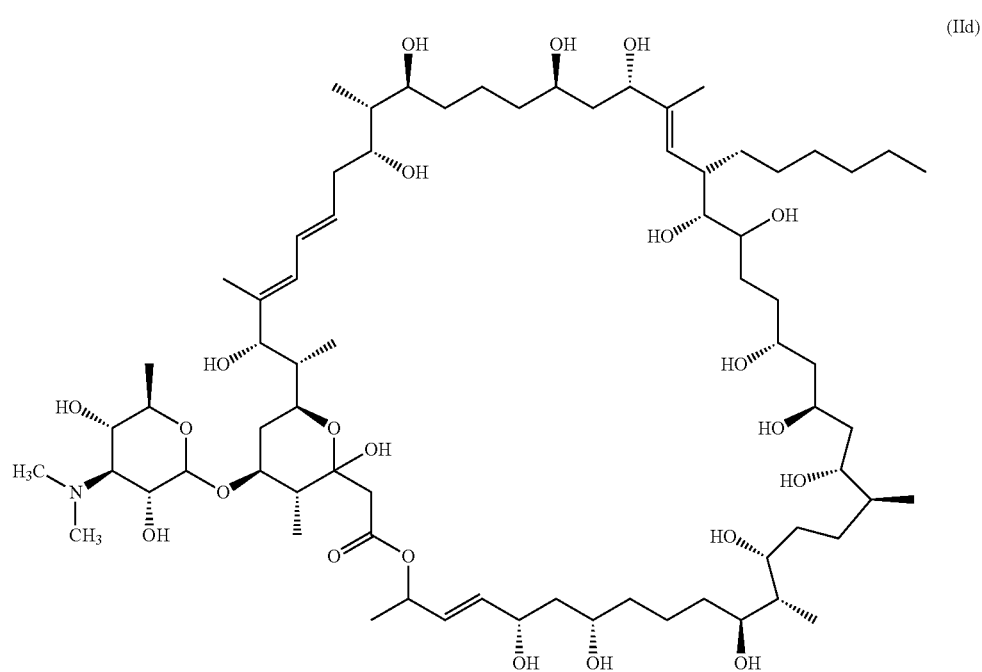
(IId)

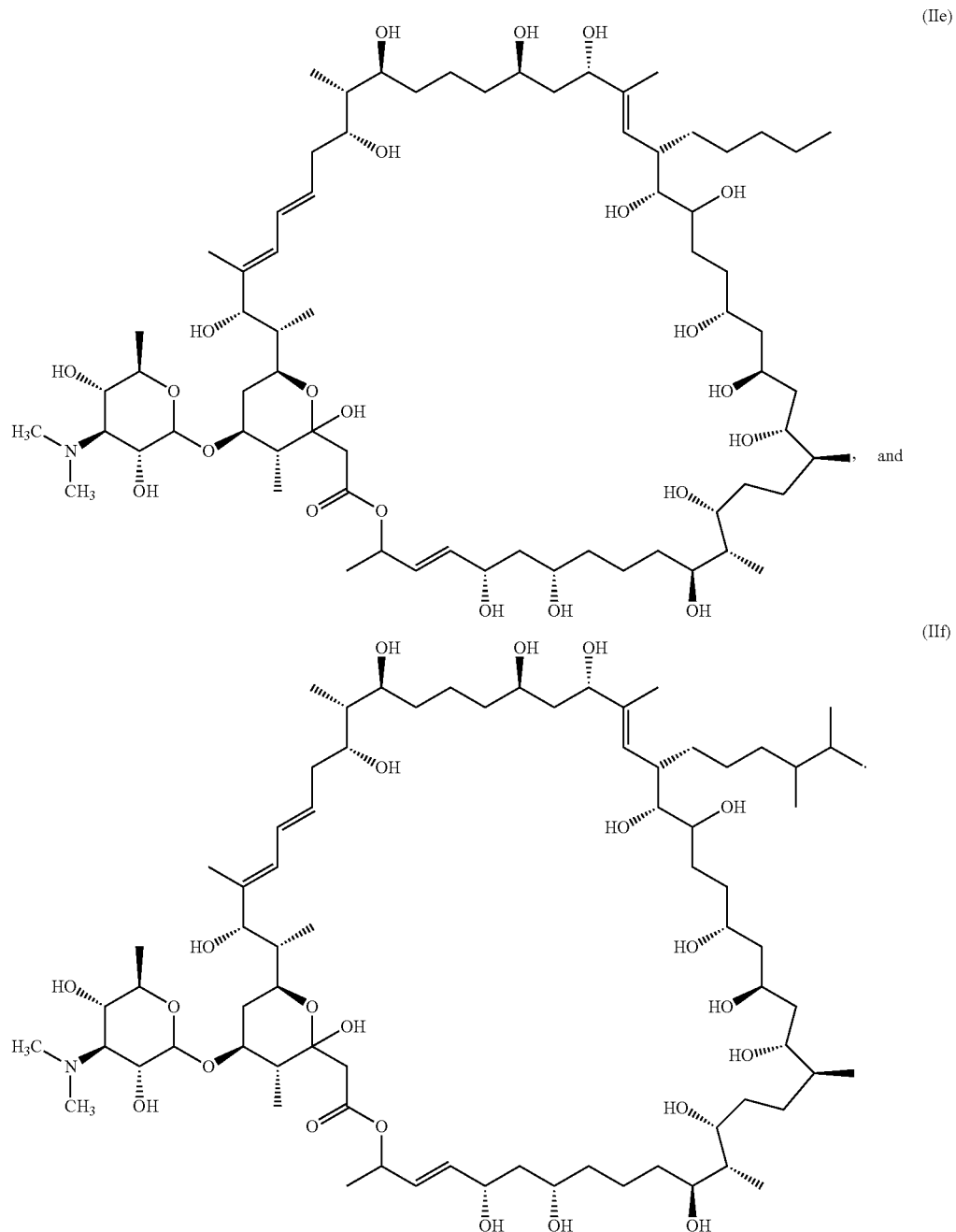

The compounds represented by the formula IIa-IIf are novel and have been named by the Inventors Stambomycin A (IIa), Stambomycin B (IIb), Stambomycin C (IIc), Stambomycin D (IId), Stambomycin E (IIe) and Stambomycin F (IIf).

The invention also relates to a process for producing the compounds defined above, comprising a step of activating the silenced large type I polyketide synthase (PKS) gene cluster of a microorganism preferably belonging to the family of Streptomycetaceae:

either by artificially over-expressing a transcriptional activator, or by culturing said microorganism in a specific medium allowing the expression of said transcriptional activator at a level sufficient to activate the expression of the biosynthetic genes.

said transcriptional activator being encoded by a gene belonging to said type I PKS gene cluster, said type I PKS gene cluster being preferably located at about 500 kbp from the end of the right arm of the chromosome of said microorganism, and said microorganism being preferably *Streptomyces ambofaciens*, in particular *Streptomyces ambofaciens* deposited at the American Type Culture Collection under the number ATCC 23877.

Other advantageous *Streptomyces ambofaciens* strains such as *Streptomyces ambofaciens* deposited at the German Collection of Microorganisms and Cell Cultures (DSMZ— Deutsche Sammlung von Mikroorganismen and Zellkulturen GmbH, Inhoffenstraβe 7 B 38124 Braunschweig GERMANY) under the number DSM 40697, or at ATCC under the deposit number ATCC15154, can be used to produce compounds according to the invention.

According to the invention, the phrase "allowing the expression of said transcriptional activator at a level sufficient to activate the expression of the biosynthetic genes." means that said expression would be sufficient to cause production of the metabolic products of the genes. On the contrary in standard medium, the inventors hypothesized that either the transcriptional activator is unexpressed or is expressed at a level insufficient to activate the expression of the biosynthetic genes.

An advantageous embodiment of the invention relates to a process for producing the compounds defined above, comprising a step of activating the silenced large type I polyketide synthase (PKS) gene cluster of *Streptomyces ambofaciens*, in particular *Streptomyces ambofaciens* deposited at the American Type Culture Collection under the number ATCC 23877:
  either by artificially over-expressing a transcriptional activator,
  or by culturing said microorganism in a specific medium allowing the expression of said transcriptional activator, at a level sufficient to activate the expression of the biosynthetic genes.
said transcriptional activator being coded by a gene belonging to said type I PKS gene cluster,
said type I polyketide synthase (PKS) gene cluster being preferably located at about 500 kbp from the end of the right arm of the chromosome of said *Streptomyces ambofaciens* deposited at the American Type Culture Collection (ATCC: Patent Depository, 10801 University Blvd. Manassas, Va. 20110, USA) under the number ATCC 23877.

As mentioned above, the invention relates to a process that allows the production of compounds having formula (I) and (I-A), formula (II) and (II-A), or at least one of the compounds having the formula IIa, IIb, IIc, IId, IIe or IIf.

The process according to the invention comprises a step of activating a silenced type I PKS gene cluster. Indeed, the process according to the invention is based on the characterization of the genes that belong to a new PKS gene cluster: the Stambomycin cluster. The Stambomycin cluster is detailed in Example 1.

The inventors have observed that the Stambomycin cluster is silenced, which means that all or most of the biosynthetic genes that compose said Stambomycin cluster are not, or substantially not expressed in the wild type microorganism, under standard laboratory culture conditions. It is well known in the art that genes that are not expressed means that the DNA sequence is not transcribed into RNA, and thus said RNA cannot be translated into protein. The consequence of the silencing of the said Stambomycin cluster is that the secondary metabolites that can be biosynthesised by the said Stambomycin cluster are not produced.

The inventors have unexpectedly observed that, if said Stambomycin cluster is unlocked, i.e. if said cluster is activated, i.e. if each biosynthetic gene of said Stambomycin cluster is expressed, then the microorganism containing said Stambomycin cluster is able to produce new compounds: the compounds according to the invention.

In the invention the generic terms "unlock" and "activation" will be used uniformly to refer to the activation of the cluster.

During the characterization of the cluster the Inventors have identified a transcriptional activator that could govern the expression of almost all or all the genes contained in the cluster. Indeed, in microorganisms, some genes that are involved in the same signalling pathway, the same biosynthesis pathway or the same degradation pathway, are often grouped in the genome of said microorganism in a genetic entity called a cluster, said cluster containing at least one operon. Said genetic unit contains the genes coding for the proteins or enzymes involved in a signalling pathway, a biosynthesis pathway, a degradation pathway, but also genes that code for regulatory proteins (activators or repressors) and specific coding sequences involved in said regulation.

Thus, for instance, when a microorganism cannot biosynthesize a molecule, the cluster containing the genes that govern the proteins or enzymes involved in said biosynthesis is silenced, i.e. all or most of the genes of the cluster are not expressed. On the contrary, when a microorganism produces a molecule, the cluster is unlocked, then genes contained in said cluster are expressed and finally the molecule is biosynthesized.

The inventors have discovered that the expression of a transcriptional activator contained in the Stambomycin cluster is sufficient to unlock said Stambomycin cluster.

The type I PKS gene cluster according to the invention, to which the Stambomycin cluster belongs, is advantageously found in microorganisms belonging to the family of Streptomycetaceae, a family of bacteria comprising the genus *Streptomyces* said genus comprising *S. achromogenes*, *S. ambofaciens*, *S. aureofaciens*, *S. avermitilis*, *S. clavuligerus*, *S. coelicolor*, *S. felleus*, *S. ferralitis*, *S. filamentosus*, *S. griseus*, *S. hygroscopicus*, *S. iysosuperficus*, *S. lividans*, *S. noursei*, *S. scabies*, *S. somaliensis*, *S. thermoviolaceus*, *S. toxytricini*, *S. tsukubaensis*, *S. venezuelae*, *S. violaceoruber*.

One advantageous microorganism according to the invention is *Streptomyces ambofaciens* and in particular the strains of *Streptomyces ambofaciens* deposited at the ATCC under the deposit number ATCC 23877 and ATCC15154, *Streptomyces ambofaciens* deposited at the DSMZ under the deposit number DSM 40697 and ETH9427 and ETH11317 strains from Eidgenössische Technische Hochschule (Zürich-Switzerland).

In the above mentioned microorganisms according to the invention, the type I PKS gene cluster, or Stambomycin cluster, is preferably located at about 500,000 base pairs (500 kbp) from the end of the right arm of the chromosome. Indeed, in contrast to most other bacteria, *Streptomyces* have a linear chromosome. From the chromosome linearity, the skilled person can easily determine the right arm of the chromosome.

In the art, *Streptomyces* bacteria are commonly cultured in a medium allowing their growth, said medium being not specifically adapted to the production of secondary metabolites.

For the production of secondary metabolites such as macrolides, specific media are used, such as MP5 or HT for spiramycin production in *Streptomyces ambofaciens*.

The Inventors have noticed that culturing *Streptomyces ambofaciens* in MP5 medium does not activate the biosynthetic genes of the Stambomycin cluster.

Unexpectedly, when *Streptomyces ambofaciens* is cultured in a medium not commonly used for the production of spiramycin (the other macrolide antibiotic produced by *S. ambofaciens*) the Stambomycin cluster is unlocked, and thus the compounds mentioned above are produced. Said medium is in particular R2 medium. The composition of R2 medium is disclosed in Example 1, and the protocol to obtain the compounds according to the invention by growing *Streptomyces* is described in Example 6.

The Inventors have also found that a transcriptional activator of said Stambomycin cluster is expressed when bacteria are cultured in said R2 medium, at a sufficient level to produce biologically active compounds.

Thus, the Inventors have transformed *Streptomyces* bacteria in order to obtain *Streptomyces* bacteria constitutively expressing the transcriptional activator, even if said *Streptomyces* is cultured in a medium that does not allow the production of macrolides. They have then identified that said *Streptomyces* produce the compounds according to the invention.

Thus, to sum up, for carrying out the process according to the invention, and produce the compounds according to the invention, the Stambomycin cluster can be unlocked by either culturing *Streptomyces* in a medium that is not commonly used for the production of macrolides, such as R2 medium or artificially over expressing a transcriptional activator contained in said Stambomycin cluster.

In one advantageous embodiment, the invention relates to a process previously defined, wherein said step of activation is carried out by over expressing a transcriptional activator belonging to the LAL family, preferably said transcriptional activator being not, or substantially not, expressed, by said microorganism under normal conditions.

The term "under normal conditions" refers in the invention to the conditions used for the proliferation of *Streptomyces*. Normal conditions are different from conditions allowing the productions of secondary metabolites such as macrolides.

The LAL family corresponds to a family of transcription factors, which was found to have an active role in the induction of expression of some type I PKS clusters, for example PikD for pikromycin production and RapH for rapamycin production (Wilson et al. 2001, *J Bacteriol* 183: 3468-3475; Anton et al. 2004, *J Bacteriol* 186: 2567-2575; Kuscer et al. 2007, *J Bacteriol* 189: 4756-4763).

Another advantageous embodiment of the invention relates to a process defined above, wherein said transcriptional activator comprises or consists of the amino acid sequence SEQ ID NO: 1.

Said transcription factor characterized in that it comprises or consists of the amino acid sequence SEQ ID NO: 1 and is coded by the nucleic acid molecule comprising or constituted by the nucleic acid sequence SEQ ID NO: 2.

Another advantageous embodiment of the invention relates to a process as defined above, further comprising a step of isolating the compounds described above.

The step of isolation of the compounds can be carried out by routine protocols commonly used by a skilled person. An example of such a protocol is disclosed in the Examples section.

Another advantageous embodiment of the invention relates to a process as defined above, further comprising a step of purifying said compounds.

The step of purification of the compounds according to the invention can be carried out by routine protocols commonly used by a skilled person. An example of such a protocol is disclosed in the Examples section.

Another advantageous embodiment of the invention relates to a process for producing the above mentioned compounds comprising:

a step of activating the silenced large type I polyketide synthase (PKS) gene cluster of *Streptomyces ambofaciens*, in particular *Streptomyces ambofaciens* deposited at the ATCC under the number ATCC 23877 by artificially over-expressing the transcriptional activator comprising or consisting of SEQ ID NO:1, a step of isolating the compounds described above, and a step of purifying the compounds isolated in the previous step.

said type I polyketide synthase (PKS) gene cluster being preferably located at about 500 kbp from the end of the right arm of the chromosome of said *Streptomyces ambofaciens* deposited at the ATCC under the number ATCC 23877.

The process according to the invention may comprise, before the step of activating the silenced large type I polyketide synthase (PKS) gene cluster, a step of adding specific substrates.

The process according to the invention may also include biological modifications of the compounds produced by the microorganism before the step of isolation and/or chemical modifications after the step of purification.

All these methods are well known to the skilled person and belong to his general knowledge.

The step of activating described above can be carried out by introducing in said *Streptomyces* an expression vector comprising the nucleic acid sequence SEQ ID NO:2, said sequence SEQ ID NO:2 being placed under the control of constitutive regulatory elements, i.e. a strong promoter.

Such vector can be integrated by site-specific recombination in the genome of said *Streptomyces*.

The above mentioned step of isolating the compounds produced by said microorganism defined above can be achieved as described in the Examples section, by isolating compounds from mycelia, when said microorganism is cultured in MP5 liquid medium or on MP5 solid medium.

An alternative corresponds to the isolation of said compound from the medium when said microorganisms are cultured on HT supplemented with 15 mM $MgCl_2$.

Another advantageous embodiment of the invention relates to a process for producing the above mentioned compounds comprising:

a step of culturing of *Streptomyces ambofaciens*, in particular *Streptomyces ambofaciens* deposited at the ATCC under the number ATCC 23877, in a specific medium allowing the expression of the transcriptional activator at a level sufficient to activate the expression of the biosynthetic genes comprising or consisting in SEQ ID NO:1, such as R2 medium a step of isolating the compounds described above, and a step of purifying the compounds isolated in the previous step.

said type I polyketide synthase (PKS) gene cluster being preferably located at about 500 kbp from the end of the right arm of the chromosome of said *Streptomyces ambofaciens* deposited at the ATCC under the number ATCC 23877.

The invention also relates to a modified microorganism producing the compounds previously defined, preferably said modified microorganism being obtained by permanently expressing a transcriptional activator in a natural microorganism, said transcriptional activator being substantially not, or not, expressed in said natural microorganism.

The invention encompasses microorganisms liable to be used for industrial production of the compounds according to the invention. The above microorganisms can be selected from bacteria, including Actinobacteria, such as Actinomycetales, and yeasts, such as *Saccharomyces cerevisiae, Schizosaccharomyces pombe* or *Pichia pastoris*, which are easy to grow in a fermentor. The microorganism according to the invention can also be *Streptomyces* species strains, including *Streptomyces ambofaciens*.

For the production of Stambomycin compounds in bacteria and yeast, the organisms have to be transformed with a vector containing the Stambomycin cluster.

This cluster, having a size of approximately 150 kbp can be easily cloned into Bacterial Artificial chromosomes (BACs), or Yeast Artificial Chromosomes (YACs) which are respectively replicative vectors allowing the transfer of foreign sequences into bacteria or yeast.

Bacteria transformed with a BAC containing the Stambomycin cluster can also be transformed with another vector allowing the expression of transcription factors allowing, or enhancing the expression of the Stambomycin cluster genes contained in the BAC.

Yeast transformed with a YAC containing the Stambomycin cluster can also be transformed with another vector allowing the expression of transcription factors allowing, or enhancing the expression of the Stambomycin cluster genes contained in the YAC.

The above transcription factor is preferably a transcriptional activator being substantially not, or not, expressed in said natural microorganism.

The skilled person has the common knowledge to select specific bacteria or yeast containing BACs or YACs, and vectors containing transcription factors, by using genetic markers (antibiotic resistance genes, susceptibility to drugs, color selection, auxotrophy etc). These procedures are routine for a person having ordinary skills in the art of genetics.

From bacteria or yeast, the skilled person, by culturing the transformed microorganisms in appropriate culture medium, can easily purify the Stambomycin compounds produced by referring to the example section.

The process of purification described in Example 2 is transposable mutatis mutandis to transformed bacteria or yeast.

According to the invention, the phrase "transcriptional activator being substantially not, or not, expressed in said natural microorganism" means that either the transcriptional activator is expressed at a level not sufficient to allow the expression of the biosynthetic genes or not expressed in the natural microorganism.

As mentioned above, the microorganism according to the invention can be transformed by a vector comprising a nucleic acid sequence coding for a transcription factor that is able to unlock the Stambomycin cluster. Said nucleic acid sequence coding for said transcriptional factor is placed under the control of a regulatory element that allows its permanent expression, i.e. the regulatory element allows the expression irrespective of the regulatory proteins present in said microorganism. Thus, if said microorganism over expresses an inhibitor of the transcription of said transcriptional activator, the sequence of the transcriptional activator placed under the control of regulatory elements that allow its permanent expression will be insensitive to said inhibitor of transcription.

Another advantageous embodiment of the invention relates to a modified microorganism previously described, wherein said microorganism constitutively expresses genes contained in the large type I polyketide synthase (PKS) gene cluster, said type I polyketide synthase (PKS) gene cluster being preferably located at about 500 kbp from the end of the right arm of the chromosome of said microorganism, said microorganism being preferably *Streptomyces ambofaciens* deposited at the ATCC under the number ATCC 23877.

In one other advantageous embodiment, the invention relates to a modified microorganism defined above, wherein the transcriptional activator belongs to the LAL family, and in particular wherein said transcriptional activator comprises or consists of the amino acid sequence SEQ ID NO: 1.

Another advantageous embodiment of the invention relates to a modified microorganism previously described, deposited at the Collection Nationale de Culture des Microorganismes (CNCM; Institut Pasteur, 25, rue du Docteur Roux, 75014 PARIS, FRANCE) on Jul. 1, 2009, under the number CNCM-1-4175.

The strain deposited under the number CNCM-1-4175 is also called in the invention ATCC/OE484.

The exact description of the construction of the strain ATCC/OE484 is disclosed in the Examples section.

Another aspect of the invention relates to a composition comprising at least one compound defined above.

In one advantageous embodiment, the invention relates to a composition as defined above, as a drug, in particular as an antibacterial drug or an antitumor drug.

The composition according to the invention can also be a food composition, a nutraceutical composition, an agricultural composition or a composition for industrial use, such as a decontaminating composition.

The invention also relates to a pharmaceutical composition comprising at least one compound as defined above as the active ingredient, in association with a pharmaceutically acceptable vehicle.

The invention also relates to a pharmaceutical composition comprising at least one compound as defined above as the active ingredient, in association with a pharmaceutically acceptable vehicle, said composition further comprising:
either at least one antitumor compound,
or at least one antibacterial compound.

The invention also relates to a pharmaceutical composition comprising at least one compound as defined above as active ingredient, in association with a pharmaceutically acceptable vehicle, said composition further comprising at least one antitumor compound. An advantageous embodiment of the invention relates to compounds defined above, in association with at least one antitumor agent, for use as a drug intended for the treatment of cancer, said compounds and said antitumor agent being simultaneously or separately used, or used spread over time.

The invention also relates to a pharmaceutical composition comprising at least one compound as defined above as active ingredient, in association with a pharmaceutically acceptable vehicle, said composition further comprising at least one antibacterial compound.

An advantageous embodiment of the invention relates to compounds defined above, in association with at least one antibacterial agent, for use as drugs intended for the treatment of bacterial infections, said compounds and said antibacterial agent being simultaneously or separately used, or used spread over time.

Dosage of the active substance depends on the administration route, and can be easily determined by a skilled person. The pharmaceutical composition according to the invention can be administered by intravenous route, sub-cutaneous route, systemic route, or can be administered locally by infiltration, or per os.

The pharmaceutical composition according to the invention can be administered at a dosage from about 0.1 g/kg/day to about 10 g/kg/day, according to the administration route.

In particular, the pharmaceutical compositions according to the invention may be administered at a dosage from about 2 to about 5 g/day in adults, or from about 50 mg to about 100 mg/kg/day for children.

"Antitumor compound" means in the invention any compounds having an activity which inhibit cell proliferation, or enhance apoptosis of tumour cells. These compounds are called chemotherapeutic agents. The skilled person can easily determine from the pathology which antitumor compound can be added to the compounds according to the invention.

"Antibacterial compound" means, in the invention, any antibiotic having bacteriostatic (inhibition of cell growth) or bactericidal (cell death) properties on bacteria.

The invention also relates to compounds defined above, for use as a drug intended for the prevention or the treatment of:
- pathologies associated with microbial infection, in particular bacterial, fungal or parasitic infections, and/or
- pathologies associated with abnormal cellular proliferation, including cancer.

In the invention, pathologies associated with microbial infection can be, for instance, sepsis, septicaemia, nosocomial disease, including *Staphylococcus aureus* infection, Lyme disease, celulitis, osteomylitis, syphilis, meningitis or plague. Microbial infections also encompass in the invention viral infections.

In the invention, pathologies associated with parasitic infection can be, for instance, infections caused by metazoa or protozoa living in the human body and causing symptoms. For instance, parasites can be plasmodies, taenia, leshmanias, etc.

Pathologies associated with abnormal cellular proliferation correspond to pathologies wherein cells grow indefinitely, without senescence. The cells are then considered as "immortalized". These pathologies include cancer, in particular metastatic cancer, such as lung cancer, breast cancer, prostate cancer, bladder cancer, intestinal cancer, colon cancer, skin cancer, brain cancer. The cancers according to the invention also include myeloproliferative and lumphoproliferative diseases, leukaemia, lymphoma.

The invention also relates to the use of compounds as defined above, for the preparation of a drug intended for the prevention or the treatment of:
- pathologies associated with microbial infection, in particular bacterial, fungal or parasitic infections, and/or
- pathologies associated with abnormal cellular proliferation, including cancer.

Another aspect of the invention relates to a method for treating
- pathologies associated with microbial infection, in particular bacterial, fungal or parasitic infections, and/or
- pathologies associated with abnormal cellular proliferation, including cancer, said method comprising a step of administering in a patient in need thereof a therapeutically effective amount of at least one compound defined above.

An advantageous embodiment of the invention relates to compounds defined above, in association with at least one antitumor agent, for use as a drug intended for the treatment of cancer, in particular said compounds and said antitumor agents are simultaneously or separately used, or used spread over time.

An advantageous embodiment of the invention relates to compounds defined above, in association with at least one antimicrobial agent, for use as a drug intended for the treatment of microbial infections, in particular said compounds and said antimicrobial agents are simultaneously or separately used, or used spread over time.

The composition comprising compounds according to the invention and at least an antitumor agent can be delivered continuously or sequentially, by perfusion delivering said compounds continuously eventually in a constant dosage, or discontinuously by one or more daily injection or absorption, eventually repeated during many days, either consecutive, or with a delay during which no treatment is taken.

The invention also relates to compounds obtainable by the process defined above.

In other words, the invention relates to compounds obtainable by the process comprising a step of activating the silenced large type I polyketide synthase gene cluster of a microorganism preferably belonging to the family of Streptomycetaceae:
- either by artificially over-expressing a transcriptional activator,
- or by culturing said microorganism in a specific medium allowing the expression of said transcriptional activator, at a level sufficient to activate the expression of the biosynthetic genes.

said transcriptional activator being encoded by a gene belonging to said type I PKS gene cluster, said type I PKS gene cluster being preferably located at about 500 kbp from the end of the right arm of the chromosome of said microorganism, and said microorganism being preferably *Streptomyces ambofaciens*, in particular *Streptomyces ambofaciens* deposited at the ATCC under the number ATCC 23877.

In one advantageous embodiment, the invention relates to compounds obtainable by the process as defined above, said compounds being Stambomycin A, and/or Stambomycin B, and/or Stambomycin C, and/or Stambomycin D.

In one advantageous embodiment, the invention relates to compounds obtainable by the process as defined above, said compounds being Stambomycin A, and Stambomycin B, and Stambomycin C, and Stambomycin D.

Also, one advantageous embodiment of the invention relates to compounds obtainable by the process as defined above, said compounds being Stambomycin E and Stambomycin F.

Said compounds E and F are obtained from the above mentioned process in which:
- either precursors of secondary metabolites are included in the culture medium
- or by chemical or biological modifications of Stambomycin A, Stambomycin B, Stambomycin C or Stambomycin D.

The invention also relates to compounds obtainable by the process defined above, preferably said process being carried out by using the modified microorganism defined above.

The invention also relates to compounds obtainable by the process defined above, preferably said process being carried out by using a modified microorganism said modified microorganism being obtained by permanently expressing a transcriptional activator in a natural microorganism, said transcriptional activator being substantially not, or not, expressed in said natural microorganism.

The invention also relates to a method for decontaminating a surface or a biological sample, contaminated by bacteria, comprising:
- incubating the surface or the biological sample with at least one compound as defined above,
- leaving said compound killing the bacteria, and
- eventually, eliminating dead bacteria.

BRIEF DESCRIPTION OF THE DRAWINGS

The invention will be better explained by the following figures and examples. In any case, the following examples should not be considered as restricting the scope of the invention.

FIG. 2 represents the alignment of the characteristic motifs present in the KR domains. The consensus sequence at the N-termini was proposed to bind to NAD(P)H. The amino acids of the catalytic triad are marked with an asterisk. The boxed amino acids are involved in determining the stereochemistry of the polyketide. For each KR domain we propose the stereochemical configuration on the right of the alignment (Keatinge-Clay, 2007). A1=2R, 3S; A2=2S, 3S; B1=2R, 3R; B2=2S, 3R; C1=2R.

FIG. 3 represents the alignment of the characteristic motifs present in the AT domains. The amino acids of the active site, also involved in the substrate specificity are boxed. The amino acids marked with an asterisk are highly conserved. The arginine marked with a hash interacts with the carboxyl group of the precursors.

FIG. 21A represents a Petri dish wherein the effect of Stambomycins C/D has been tested on *B. subtilis* proliferation. A: corresponds to 1 µg of Stambomycins C/D, B: corresponds to 3 µg of Stambomycins C/D, C: corresponds to 5 µg of Stambomycins C/D, D: corresponds to 10 µg of Stambomycins C/D.

FIG. 21B represents a Petri dish wherein the effect of Stambomycins A/B has been tested on *B. subtilis* proliferation. A: corresponds to 1.25 µg of Stambomycins A/B, B: corresponds to 2.5 µg of Stambomycins A/B, C: corresponds to 10 µg of Stambomycins A/B, D: corresponds to 12.5 µg of Stambomycins A/B.

FIG. 22A represents a Petri dish wherein the effect of Stambomycins C/D has been tested on *M. luteus* proliferation. A: corresponds to 1 µg of Stambomycins C/D, B: corresponds to 3 µg of Stambomycins C/D, C: corresponds to 5 µg of Stambomycins C/D, D: corresponds to 10 µg of Stambomycins C/D.

FIG. 22B represents a Petri dish wherein the effect of Stambomycins A/B has been tested on *M. luteus* proliferation. A: corresponds to 1.25 µg of Stambomycins A/B, B: corresponds to 2.5 µg of Stambomycins A/B, C: corresponds to 10 µg of Stambomycins A/B, D: corresponds to 12.5 µg of Stambomycins A/B.

FIG. 27A represents the base peak of ATCC/OE484 grown in liquid R2 medium.

FIG. 27B represents the base peak of ATCC23877 grown in liquid R2 medium.

The peaks, with retention times of approximately 19 min, correspond to Stambomycins A/B.

Figure 27:
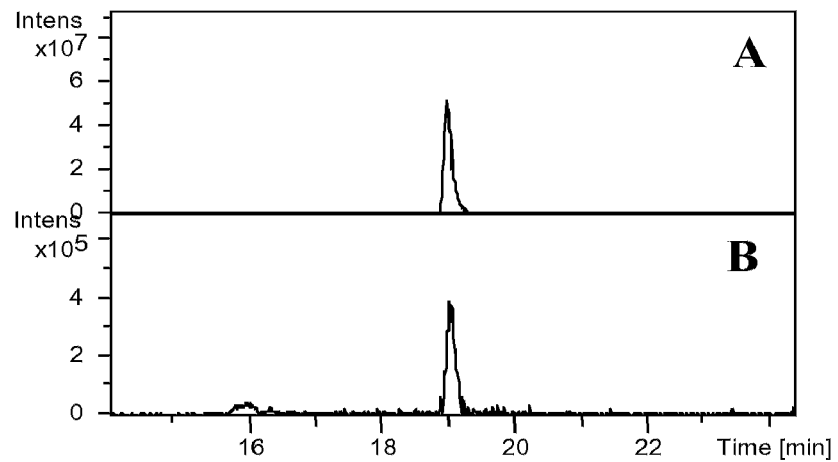
FIGS. 27 A and B represent the LC-MS base peak chromatogram for extracts from the strain ATCC/OE484 and ATCC23877.
Figure 28:
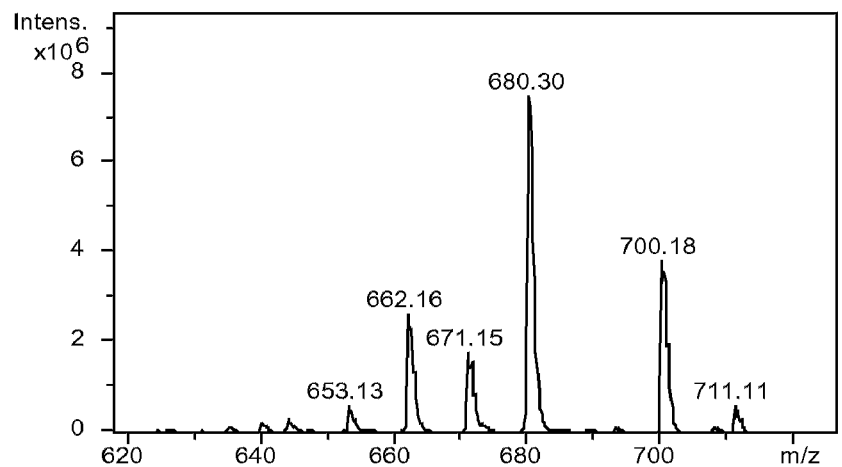

FIG. 28 represents mass spectra of compounds indicated in FIG. 27B. The ion with m/z=680 corresponds to the doubly charged parent ions $(M+2H)^{2+}$ of Stambomycins A/B. The X-axis represents mass/charge (m/z) and the Y-axis represents ion intensity $\times 10^6$, expressed in arbitrary units.

Figure 29:
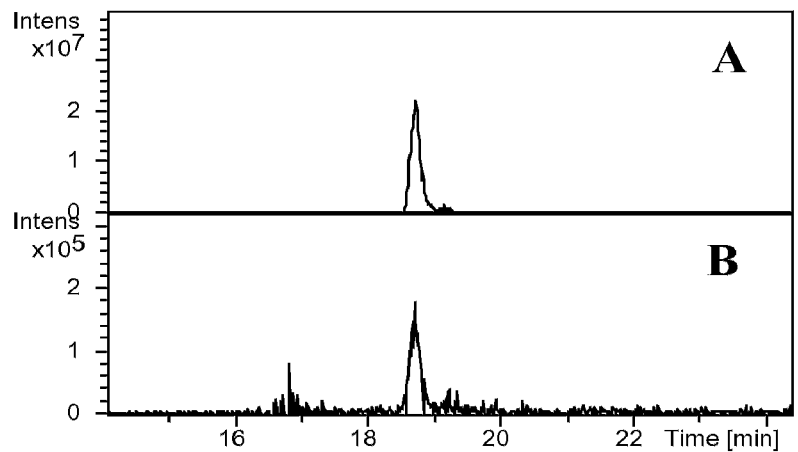

FIGS. 29 A and B represent the LC-MS base peak chromatogram for extracts from the strain ATCC/OE484 and ATCC23877.

FIG. 29A represents the base peak of ATCC/OE484 grown in liquid R2 medium.

FIG. 29B represents the base peak of ATCC23877 grown in liquid R2 medium.

The peaks, with retention times of approximately 19 min, correspond to Stambomycins C/D.

Figure 30:
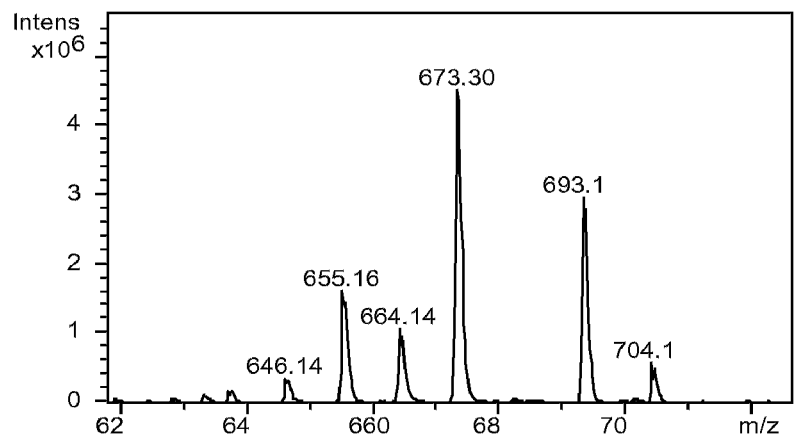

FIG. 30 represents mass spectra of compounds indicated in FIG. 29B. The ion with m/z=673 corresponds to the doubly charged parent ions $(M+2H)^{2+}$ of Stambomycins C/D. The X-axis represents mass/charge (m/z) and the Y-axis represents ion intensity $\times 10^6$, expressed in arbitrary units.

Figure 31:
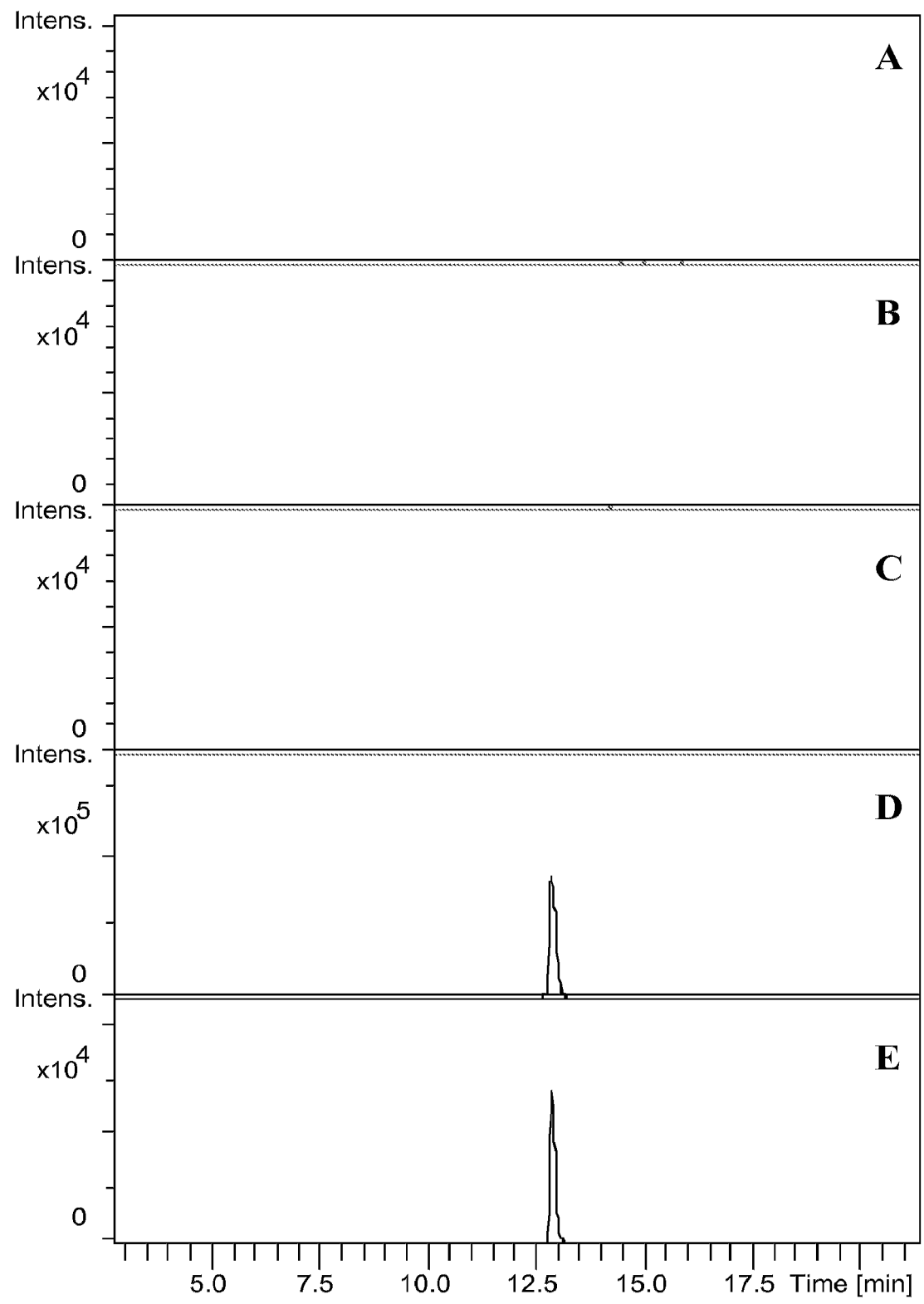

FIGS. 31A, B, C, D and E represent the LC-MS extracted ion chromatograms for mycelium extracts from the strains grown in liquid R2 medium.

FIG. 31A represents the extracted ion chromatogram of ATCC23877 in which the SAMR0467 ORF is deleted.

FIG. 31B represents the extracted ion chromatogram of ATCC23877 in which the SAMR0484 ORF is deleted.

FIG. 31C represents the extracted ion chromatogram of ATCC/OE484 in which the SAMR0467 ORF is deleted.

FIG. 31D represents the extracted ion chromatogram of ATCC/OE484.

FIG. 31E represents the extracted ion chromatogram of ATCC23877.

The peaks, with retention times of approximately 12.5 min, correspond to Stambomycins A/B.

Figure 32:
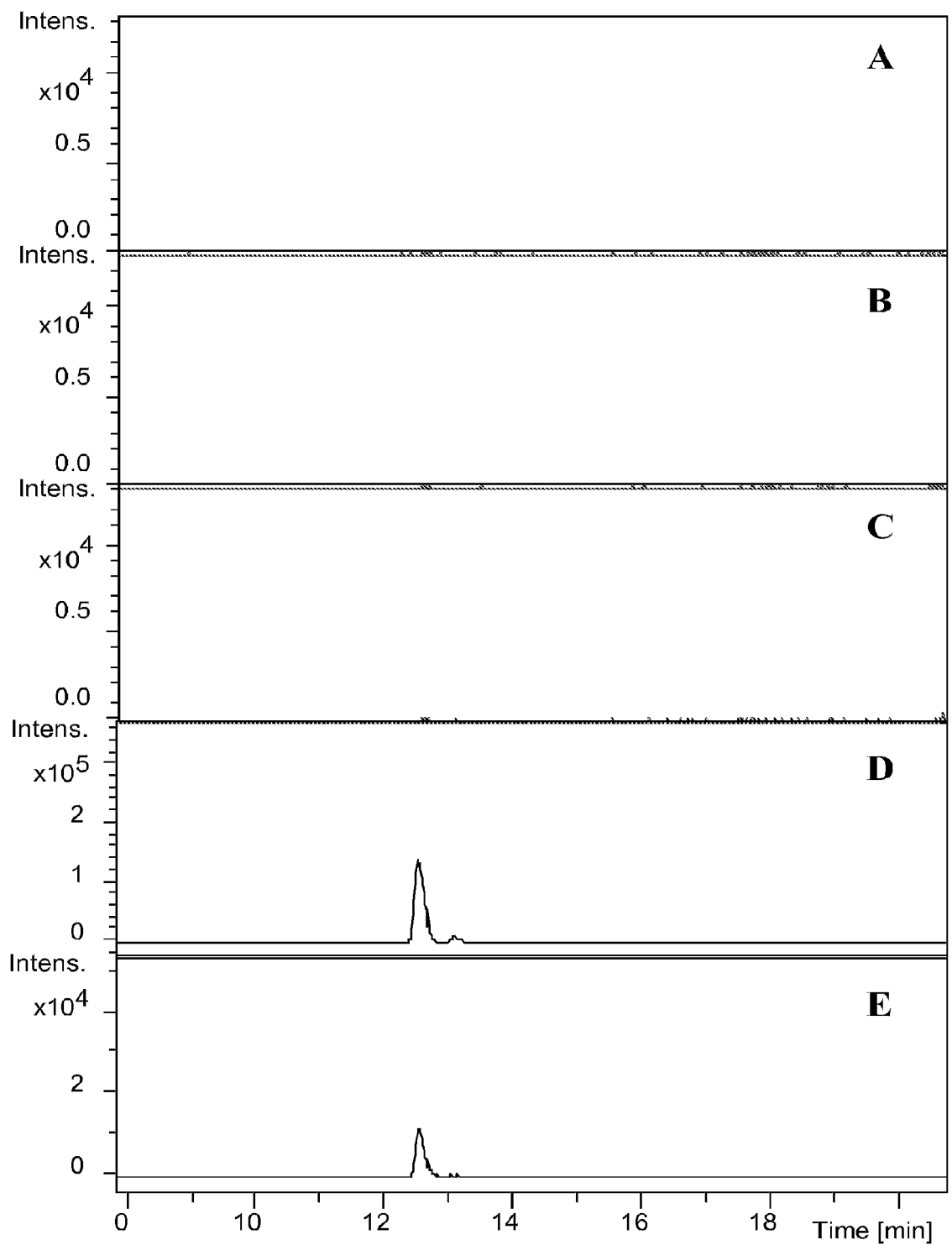

FIGS. 32A, B, C, D and E represent the LC-MS extracted ion chromatogram for mycelium extracts from the strains grown in R2 medium.

FIG. 32A represents the extracted ion chromatogram of ATCC23877 in which the SAMR0467 ORF is deleted.

FIG. 32B represents the extracted ion chromatogram of ATCC23877 in which the SAMR0484 ORF is deleted.

FIG. 32C represents the extracted ion chromatogram of ATCC/OE484 in which the SAMR0467 ORF is deleted.

FIG. 32D represents the extracted ion chromatogram of ATCC/OE484.

FIG. 32E represents the extracted ion chromatogram of ATCC23877.

The peaks, with retention times of approximately 12.5 min, correspond to Stambomycins C/D.

EXAMPLES

Example 1

Composition of the R2 Medium

The R2 medium is prepared as follows: in 800 mL of distilled water Sucrose 103 g, $K_2SO_4$ 0.25 g, $MgCl_2$ $6H_2O$ 10.12 g, Glucose 10 g and Difco casaminoacids 0.1 g are dissolved. The solution is sterilized for 20 min at 120° C.

Then the following are added: 10 mL of $KH_2PO_4$ (0.5%), 80 mL of $CaCl_2$ $2H_2O$ (3.68%), 15 mL of L-proline (20%), 100 mL of TES buffer (5.73%, adjusted to pH 7.2), 2 mL of Trace element solution and 5 mL of NaOH (1M).

The trace element solution contains $ZnCl_2$ 40 mg, $FeCl_3$ $6H_2O$ 200 mg, $CuCl_2$ $2H_2O$ 10 mg, $MnCl_2$ $4H_2O$ 10 mg, $Na_2B_4O_7$ $10H_2O$ 10 mg and $(NH_4)_6Mo_7O_{24}$ $4H_2O$ 10 mg in 1 L of distilled water.

For preparation of plates, 22 g of Difco Bacto agar are added to the 800 mL of solution prior to sterilization.

Example 2

Activation of the Silent Modular Polyketide Synthase Gene Cluster in *Streptomyces ambofaciens*

Methods

Bacterial Strains, BACs, Plasmids

*Streptomyces ambofaciens* ATCC23877 was the reference strain for all the experiments (Pinnert-Sindico et al., 1954 cited above). *Escherichia coli* DH5α was used for routine cloning (Hanahan, D. *J Mol Biol*, 1983, 166: 557-580); *E. coli* ET12567/pUZ8002 was used for intergenic conjugation with *Streptomyces* (MacNeil et al., *Gene*, 1992, 111: 61-68; Paget et al. *J Bacteriol*, 1999, 181: 204-211). The pGEMT-easy (Promega) and pIB139 (Wilkinson et al., *J Mol Microbiol Biotechnol*, 2002, 4: 417-426) vectors were used for cloning and overexpression.

Media and Growth Conditions

Luria-Bertani (LB) medium was used for *E. coli* growth, as well as for *Bacillus subtilis* and *Micrococcus luteus*. All *E. coli* strains were grown at 37° C. For spore production, *Streptomyces* strains (ATCC23877, ATCC15154, DSM40697 and CNCM-1-4175) were grown on SFM at 30° C., while for conjugation SFM was supplemented with 10 mM $MgCl_2$ (Kieser et al, 2000 *Practical streptomyces genetics*. Norwich). Genomic DNA was isolated from cultures grown in HT at 30° C.; YEME 34% was used to grow cultures for pulsed-field gel electrophoresis analysis. Growth curves and cultures for RNA isolation were performed in HT or MP5 (Pernodet et al., *J Gen Microbiol*, 1993, 139: 1003-1011.) media at 30° C. LC-MS and HPLC samples were always obtained from cultures grown on or in MP5 for at least three days. When needed the following antibiotics were added into the cultures: apramycin, nalidixic acid (both at 25 μg/mL).

DNA Manipulation

Plasmids were extracted from *E. coli* by the alkaline lysis method (Sambrook et al. 1989, Molecular cloning: A laboratory manual Cold Spring Harbor Laboratory Press, New York). Genomic DNA from *Streptomyces* was isolated as already described (Leblond et al. *Mol Microbiol*, 1996, 19: 261-271). Southern blots were performed with a Hybond-N nylon membrane (Amersham-Pharmacia) and a vacuum transfer system (BioRad), as previously described (Pang *Antimicrob Agents Chemother*, 2004, 48: 575-588). Preparation of chromosomal DNA for analysis by pulsed-field gel electrophoresis was performed essentially as described by Leblond et al (1996 cited above).

Amplification of DNA fragments by PCR was performed with Taq DNA polymerase (NEB) or Takara polymerase (Fermentas), according to the manufacturer's instructions. PCR products and restriction fragments were purified from agarose gels with the High Pure PCR product purification kit (Roche).

Overexpression of SAMR0468-9 and SAMR0484

The coding sequences of SAMR0468-9 (1971 bp) and SAMR0484 (2877 bp) were amplified by PCR from the wild type strain of *S. ambofaciens* ATCC 23877, with the primers OE468-F and OE469-R, and with the primers OE484-F and OE484-R, respectively, which contain the restriction sites for NdeI and XbaI (see Table 1). The PCR products were gel purified and cloned into pGEMT-easy (Promega). The integrity of the coding sequences was checked by sequencing. The vectors pGEMT-468-9 and pGEMT-484 were digested using NdeI and XbaI; the inserts were gel purified and cloned into a modified version of the plasmid pIB139, digested using the same enzymes. The ORFs are under the control of the strong and constitutive promoter ermEp* which was previously modified to have a typical *Streptomyces* ribosome binding site (AAAGGAGG) (Bunet et al, *J Bacteriol* 2008, 190: 3293-3305). The recombinant vectors pOE468-9 and pOE484 were introduced by conjugation into *S. ambofaciens* ATCC 23877 in which they integrated by site specific recombination with the attB site of the chromosome. All the mutants were analysed by PCR, Southern Blot and PFGE, to ensure the desired modification had occurred.

The strain over expressing SAMR0484 corresponds to the strain deposited at the CNCM under the deposit number CNCM I-4175.

| SEQ ID NO: | | Primers sequence (5'→3') Nucleotide |
|---|---|---|
| Overexpression: | | |
| SEQ ID NO: 3 | OE468-F | AGGTCTAGAGTCAGCCGAGGAAAC |
| SEQ ID NO: 4 | OE469-R | CATATGACGAACGTGTCACGCGCGC |
| SEQ ID NO: 5 | OE484-F | CATATGCTGGTCCATCGAGACGAAC |
| SEQ ID NO: 6 | OE484-R | TCTAGACTCTGCTCTCTCCAAGGCT |
| Transcriptional analysis: | | |
| SEQ ID NO: 7 | hrdB-F | CGCGGCATGCTCTTCCT |
| SEQ ID NO: 8 | hrdB-R | AGGTGGCGTACGTGGAGAAC |
| SEQ ID NO: 9 | RT-467-F | GTCGCCGGATCACCGAGGAA |
| SEQ ID NO: 10 | RT-467-R | AGGTCGCGGAACGCCTTGTC |
| SEQ ID NO: 11 | RT-465-F | TGCCTGCGGTGCTCCACCAA |
| SEQ ID NO: 12 | RT-465-R | CGTCGTCTTCTCCTCCATCG |
| SEQ ID NO: 13 | RT-474-F | ACCGCGCCGGAGGTGAGACA |
| SEQ ID NO: 14 | RT-474-R | GCTGCTCGCCTGCGTGGACA |
| SEQ ID NO: 15 | RT-477-F | GGAACAGCTCGCCGTACTCC |
| SEQ ID NO: 16 | RT-477-R | CCGAACTCGTCGGCGTATGG |
| SEQ ID NO: 17 | RT-484-F | CTGGAGACCTTCGGGGAGTG |
| SEQ ID NO: 18 | RT-484-R | TGCCCGAGCACTCCGAAATG |

Table 1 lists the oligonucleotides used in the invention. The underlined sequences correspond to the XbaI or NdeI sites.

Transcriptional Analysis

Total RNA of *Streptomyces* ATCC23877 wild type and mutant strains was isolated from MP5 or HT liquid cultures at different time points of the growth curve, and treated as described by Kieser et al (2000 cited above). cDNAs were obtained as already described by Bunet et al. (2008 cited above).

The primer pairs used to analyse the expression of the genes in the PKS cluster are listed in Table 1. They were designed to amplify an internal region of about 100 bp, at the beginning of the gene. PCR conditions were: 4 min at 94° C., 28 cycles of 30 s at 94° C.; 30 s at 60° C., and 30 s at 72° C., followed by a final extension of 5 min at 72° C. To check possible contamination by genomic DNA, the same PCR programme (35 cycles instead of 28) was applied to RNA samples, before reverse transcriptase treatment, using as a control, primers to amplify the hrdB gene, which encodes a major sigma factor considered to be constitutively expressed.

1—Identification and Characterization of a New Type I PKS Cluster

During the sequencing of the linear chromosome of *Streptomyces ambofaciens* ATCC23877, 12 clusters potentially associated with secondary metabolites production were identified in the terminal regions (Choulet et al., cited above). In particular, in the right arm, at 500 Kb from the end of the chromosome, a large type I polyketide synthase (PKS) cluster was found, which has been named the Stambomycin cluster. This cluster contains 25 genes and its size is about 150 Kb. The genes are listed in Table 2.

TABLE 2

Genes within the Stambomycin biosynthetic gene cluster and their proposed functions.

| ORF | Product size (aa) | % identity/ similarity | Species | Putative function | Proposed function |
|---|---|---|---|---|---|
| SAMR0465 | 8154 | | | Type I PKS | |
| SAMR0466 | 3661 | | | Type I PKS | |
| SAMR0467 | 5771 | | | Type I PKS | |
| SAMR0468 | 217 | 84/88 | *S. griseus* (SGR874) | Response regulator | Regulation |
| SAMR0469 | 442 | 77/84 | *S. griseus* (SGR875) | Histidine kinase | Regulation |
| SAMR0470 | 261 | 87/93 | *S. griseus* (SGR876) | Putative permease protein | Resistance |
| SAMR0471 | 312 | 88/93 | *S. griseus* (SGR877) | Putative ABC transporter ATP-binding protein | Resistance |
| SAMR0472 | 244 | 55/68 | *S. erythraea* | N-dimethyltransferase | Sugar biosynthesis |
| SAMR0473 | 185 | 46/59 | *S. fradiae* | Isomerase | Sugar biosynthesis |
| SAMR0474 | 6333 | | | Type I PKS | |
| SAMRCDS1 | 3556 | | | Type I PKS | |
| SAMR0475 | 3157 | | | Type I PKS | |
| SAMR0476 | 3565 | | | Type I PKS | |
| SAMRCDS2 | 1569 | | | Type I PKS | |

TABLE 2-continued

Genes within the Stambomycin biosynthetic gene cluster and their proposed functions.

| ORF | Product size (aa) | % identity/ similarity | Species | Putative function | Proposed function |
|---|---|---|---|---|---|
| SAMR0477 | 5447 | | | Type I PKS | |
| SAMR0478 | 414 | 43/62 | S. fradiae | Cytochrome P450 | Lactone ring modification |
| SAMR0479 | 401 | 41/56 | R. castenholzii | Cytochrome P450 | Lactone ring modification |
| SAMR0480 | 369 | 74/82 | Streptomyces sp. TP-A0274 | Aminotransferase | Sugar biosynthesis |
| SAMR0481 | 418 | 48/63 | M. griseorubida | Glycosyltransferase | Sugar attachment |
| SAMR0482 | 595 | 64/75 | S. hygroscopicus | Acyl-CoA synthetase | Precursor biosynthesis |
| SAMR0483 | 532 | 62/74 | S. arenicola | Carboxyl transferase | Precursor biosynthesis |
| SAMR0484 | 958 | 35/47 | S. venezuelae (PikD) | Transcriptional activator (LAL) | Regulation |
| SAMR0485 | 255 | 87/94 | S. griseus (SGR200) | Type II thioesterase | PKS editing |
| SAMR0486 | 329 | 77/84 | S. tenebrarius (AprE) | dTDP-glucose 4,6-dehydratase | Sugar biosynthesis |
| SAMR0487 | 290 | 74/85 | S. avermitilis (AveBIII) | Glucose-1-phosphate thymidyltransferase | Sugar biosynthesis |

Analyses were carried out with the BlastP programme (http://blast.ncbi.nlm.nih.gov/Blast.cgi). The best hits are indicated.

From the computational data, the Stambomycin cluster genes can be separated into four groups:

a) Biosynthetic Genes

Figure 1:
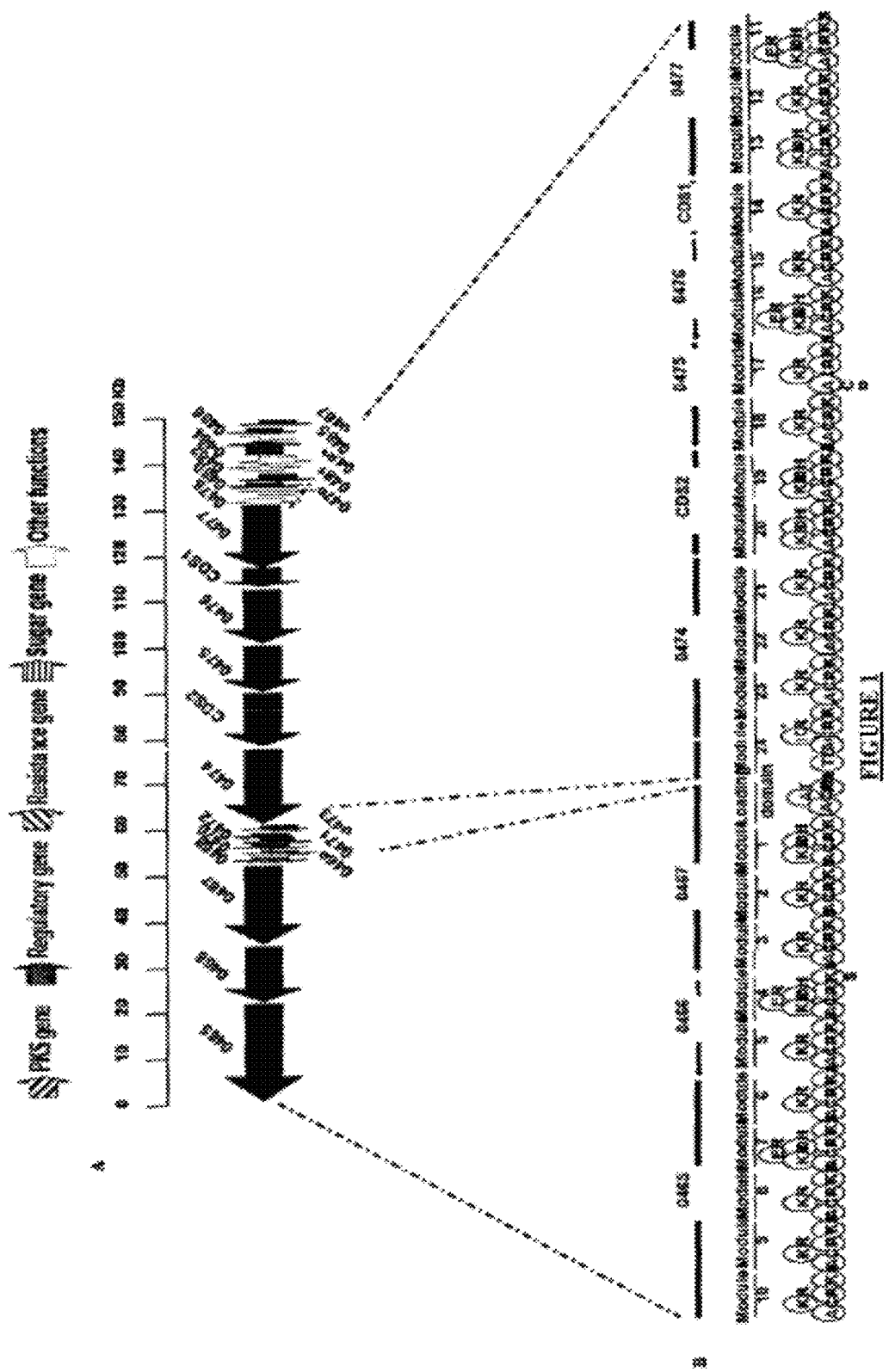
FIG. 1A represents the organisation of the Stambomycin cluster.
FIG. 1B represents the modular structure of the PKS proteins and the domain organization of the 25 modules, according to the SEARCHPKS prediction. The enzymatic domains are represented in circles: KSQ, β-ketoacyl synthase in which the active site cysteine residue is replaced by glutamine; KS, β-ketoacyl synthase; AT, acyltransferase; ACP, acyl carrier protein; KR, ketoreductase; DH, dehydratase; ER, enoyl reductase; TE, thioesterase. Inactive KR domain is marked with an asterisk.

The cluster is composed of nine giant PKS genes, whose size varies from 4.7 kbp to 24 kbp. The PKS genes are not arranged straight forwardly head to tail, but they are separated by six ORFs, (see FIG. 1). Their analysis with the program SEARCHPKS (Yadav et al. 2003 *J Mol Biol* 328: 335-363) revealed they encode a total of 25 PKS modules. All together, the PKS genes cover 124 kbp out of the 150 kbp the Stambomycin cluster spans. The Stambomycin cluster is one of the largest type I PKS gene clusters ever described in the literature.

The order in which the PKS genes interact with each other to allow the carbon chain elongation (from SAMR0467 to SAMR0465, and from SAMR0477 to SAMR0474), was established by the position of the loading domain (SAMR0467) and the TE domain (module 24 in SAMR0474). In the Stambomycin cluster, the loading domain, which is responsible for the initiation of polyketide biosynthesis, contains a particular KS domain in which the usual cysteine residue of the active site is replaced by glutamine to facilitate decarboxylation of the starter unit (Donadio and Katz, 1992, *Gene* 111: 51-60; Bisang et al., 1999, *Nature* 401: 502-505). The thioesterase is required to release the linear carbon chain of the molecule. Sequence comparisons with other TE domains suggested that, in this case, it would catalyse a cyclization reaction to give rise to a lactone ring. However, it was not possible to predict where the cyclization would occur.

In silico analyses confirmed that all the enzymatic domains, but one (see below), harbour a functional active site. Based on the AT domain sequences (Yadav et al., 2003 cited above), it was possible to predict the substrates incorporated into the polyketide backbone: the starter unit, a propionate, and the extender units (16 malonyl-CoA, 6 methylmalonyl-CoA, 1 ethylmalonyl-CoA and an unknown precursor loaded by module 12, see FIG. 3). Conserved and well characterized motifs inside the KR domain sequence (Keatinge-Clay, 2007, *Chem Biol* 14: 898-908) allowed the stereochemistry of the α-substitute and the β-hydroxyl groups derived from each precursor to be predicted, the KR domains are mostly A1 type and B1 type, with just two exceptions for KR18, which is a A2 type and KR21, which is a B2 type (see FIG. 2). The last ketoreductase domain (KR24) has an arginine and a serine instead of a tyrosine and an asparagine, respectively, in the catalytic triad (see FIG. 2). The replacement of these amino acids was shown to critically affect the activity of KR domains (Reid et al., 2003 *Biochemistry* 42: 72-79). Thus this KR domain is predicted to be no longer functional.

Since the organization of the modules reflects the chemical structure of the polyketide chain, we could predict the structure of the linear backbone of the product. The approximate mass (1120 Da) and molecular formula ($C_{61}H_{111}O_{18}$) of the molecule assembled by the PKS could be predicted.

b) Post PKS Modification Genes

The boundaries of the cluster were estimated to be from SAMR0465 to SAMR0487 according to their putative function: 16 other genes, in addition to the nine PKS genes, have been identified to be putatively involved in the biosynthesis of the compound (see Table 2). No gene encoding a 4'-phosphopantetheinyl transferase (PPTase), required for the activation of the ACP domain, by post-translational modification, was found inside or near the cluster. The same situation was observed for the spiramycin cluster (Karray et al., 2007 *Microbiology* 153: 4111-4122), suggesting that the PKSs encoded by the two clusters might share the same PPTase.

Figure 4:
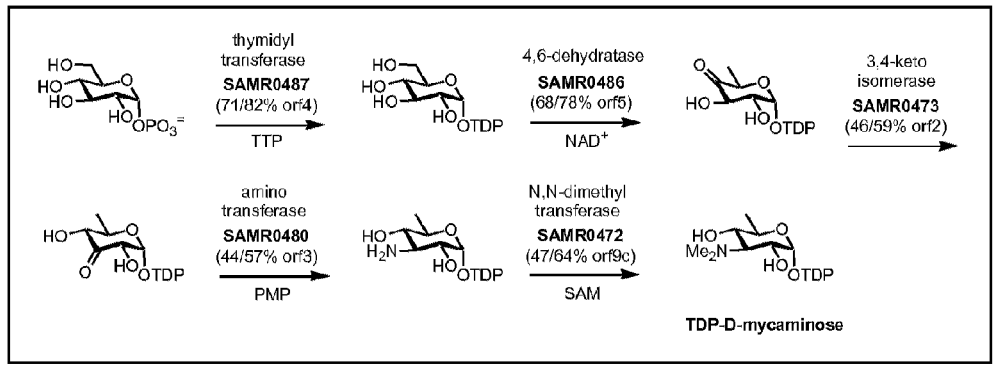
FIG. 4 represents the mycaminose biosynthetic pathway from glucose-1-phosphate. For each enzymatic step, the gene encoding for the protein involved is indicated in bold. In brackets, the percentages of identity/similarity to the spiramycin genes are indicated. Abbreviations: TTP, thymidine triphosphate; TDP, thymidine diphosphate; NAD+, nicotinamide adenine dinucleotide; PMP, pyridoxamine 5'-phosphate; SAM, S-adenosyl-L-methionine.

A glycosyltransferase (GT; SAMR0481) would be responsible for the transfer of a specific activated sugar to the lactone ring, suggesting that the final structure would be a glycoslated macrolide. The program SEARCHGTr (Kamra et al., Nucleic Acids Res., 2005, 33: W220-225) indicated a 6-deoxyhexose was the substrate of the GT, most probably an amino sugar such as desosamine or mycaminose. Sequence comparisons with the spiramycin biosynthetic gene cluster (Karray et al., 2007, cited above) (spiramycin contains two amino sugars a mycaminose and a forosamine), enabled identification of five genes (SAMR0472, SAMR0473, SAMR0480, SAMR0486 and SAMR0487) potentially involved in the conversion of glucose-1-phosphate into NDP-mycaminose (FIG. 4). Taking into account this data, we could predict the approximate mass and molecular formula of the macrolide (1322 Da;

$C_{69}H_{127}O_{22}N$). Searches in the chemical databases suggested that this structure would be novel.

Two genes (SAMR0478, SAMR0479) encoding enzymes belonging to the cytochrome P450 family were also identified. Usually these enzymes take part in hydroxylation reactions of the polyketide structure. The hydroxylation reaction catalysed by SAMR0479 seems to be directly connected with the formation of the lactone, as the structure determination showed.

The gene SAMR0482 encodes a putative acyl-CoA synthetase and SAMR0483 encodes an acyl-CoA carboxylase β domain. They are likely to be involved in the biosynthesis of a particular precursor for the polyketide synthase. SAMR0485 encodes a type II thioesterase whose function is not yet clarified. It is likely to play a role in removing aberrant groups attached to the ACP domains of the PKS, which block chain elongation (Kim et al., 2002, *J Biol Chem* 277: 48028-48034).

c) Resistance Genes

Two genes SAMR0470 and SAMR0471 encode proteins showing a significant percentage of identity (87% and 88%) respectively to an integral permease protein and an ATP-binding subunit of an ABC transporter, both from *S. griseus* (SGR876 and SGR877, respectively). Bacterial resistance by active efflux of antibiotics has been described for several macrolides (Karray et al., 2007, cited above). The proteins encoded by SAMR0470 and SAMR0471 could be involved in export of the metabolite, (not related to the resistance), as proposed by Menges et al. (*Appl Microbiol Biotechnol*, 2007, 77: 125-134).

d) Regulatory Genes

With regard to the regulation of metabolite biosynthesis, the Stambomycin cluster contains three putative regulatory genes. The gene SAMR0468 encodes a response regulator and SAMR0469 encodes a histidine kinase. Together these products form a two component system. So far only a few examples of this kind of regulator were found inside secondary metabolite biosynthetic gene cluster and have been described to control secondary metabolite biosynthesis. For example, the absA operon, associated with the cda cluster in *S. coelicolor*, was shown to negatively regulate multiple antibiotics (Anderson et al. 2001). The Stambomycin cluster also contains a "large ATP-binding LuxR family" (LAL) regulator, encoded by SAMR0484. The latter belongs to a new family recently discovered, which was found to have an active role in the onset of type I PKS cluster expression, such as PikD for pikromycin production and RapH for rapamycin production (Wilson et al. 2001 cited above; Anton et al. *J Bacteriol*, 2004, 186: 2567-2575; Kuscer et al. *J Bacteriol*, 2007, 189: 4756-4763).

2—Activation of the Stambomycin Cluster

To verify if the Stambomycin cluster was expressed in the wild type strain of *S. ambofaciens* ATCC23877, transcriptional analyses were carried out in MP5 and HT media as described in Methods. These media were initially chosen because macrolides, like spiramycin, are produced (Pernodet et al., 1993 cited above.). Under these conditions, no or very low expression of the biosynthetic genes was detected (FIG. 5), hence the Stambomycin cluster was considered to be essentially silent.

In order to trigger the expression of the Stambomycin cluster, we sought to manipulate the regulatory genes. Heterologous expression was not taken into account because of the size of the cluster.

The SAMR0468 and SAMR0469 coding sequences together (the sequences overlap, probably they are cotranscribed) and the SAMR0484 coding sequence were cloned, separately, in front of the strong and constitutive promoter ermEp* within the conjugative and integrative vector pIB139, as described in Methods (Wilkinson et al. 2002 cited above). The wild type strain of *S. ambofaciens* ATCC23877 was transformed by intergenic conjugation with the recombinant vectors and integration took place at the attB site of the chromosome. As a control, the wild type strain was also transformed with the plasmid pIB139 alone.

Figure 5:
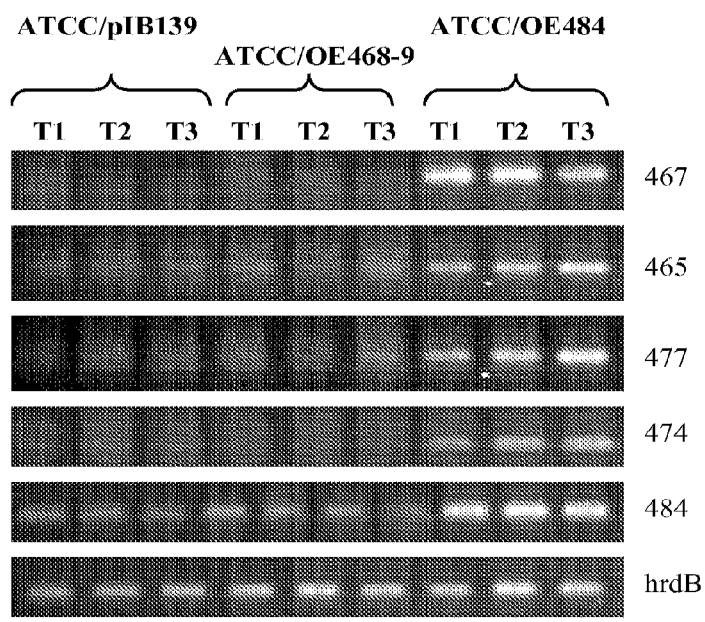
FIG. 5 represents the comparative transcriptional analysis of the control strain ATCC/pIB139 and the overexpressing mutants ATCC/OE468-9 and ATCC/OE484. The expression of four biosynthetic genes (SAMR0467, SAMR0465, SAMR0477, SAMR0474), together with the expression of the regulatory gene SAMR0484, were analysed by RT-PCR and the experiments were repeated at least three times. hrdB was used as a control. T1 corresponds to the exponential phase, T2 to the transition phase and T3 to the stationary phase.

To test the role of these genes in the regulation of the Stambomycin cluster, comparative transcriptional analyses were carried out between the regulator over-expressing and the control strains, grown in MP5 or HT media. Total RNAs were isolated from mycelium samples, taken at different time points of the growth curve (transition, exponential and stationary phase) and cDNAs were prepared as described in Methods. The expression of the PKS genes was induced by the overexpression of the LAL regulator (ATCC/OE484), thus confirming the positive role already observed for this kind of regulator (FIG. 5). On the other hand, no expression of the biosynthetic genes (i.e. SAMR0467) was detected in the ATCC/OE468-9 mutant, as well as in the control strain (ATCC/pIB139), indicating that the two component system did not act as a positive regulator, at least for the PKS genes (see FIG. 5). It remains to be clarified if the LAL regulator acts directly on the expression of the PKS genes.

3—Identification of New Metabolites Produced by *S. ambofaciens* ATCC23877

In order to examine whether the product of the Stambomycin cluster was being made, comparative metabolic profiling of the control strain ATCC/pIB139 and the mutant ATCC/OE484 was carried out. The strains were grown in MP5 medium and the samples were analysed using Liquid-Chromatography Mass Spectroscopy (LC-MS) (see Methods).

Culture extracts of both the supernatant and the mycelium were analysed. The LC-MS base peak chromatogram of the mycelium extract of the overexpressed mutant revealed two peaks, giving doubly charged ions with m/z of 673 and 680 (positive ion mode) corresponding to molecular formulae of $C_{72}H_{132}NO_{22}$ and $C_{73}H_{134}NO_{22}$, respectively. These are not present in the mycelium extract of the control strain. These data showed that the Stambomycin cluster was responsible for the production of at least two compounds, here named Stambomycins A/B and C/D respectively. No Stambomycins were detected in the supernatant, under these conditions.

However, same strains cultured on HT medium supplemented with 15 mM $MgCl_2$ presents Stambomycins A/B and C/D secretion in the culture medium.

To prove that the two molecules, corresponding to the peaks 673 and 680, arise from the Stambomycin cluster, a deletion of the first PKS gene, SAMR0467, was made in the mutant ATCC/OE484, (data not shown). The deletion of the first four modules, including the loading domain, would be expected to abolish the production of Stambomycins. Indeed, no Stambomycins were detected in the mycelium extract of this mutant.

Example 3

Elucidation of the Structure of Stambomycins

1. Isolation of Stambomycins A (IIa), B (IIb), C (IIc) and D (IId) from *S. ambofaciens*.

*Streptomyces ambofaciens* ATCC23877/OE484 (CNCM-1-4175) spores were stored in 25% (v/v) aqueous glycerol at −20° C. Solid medium containing 7 g/L yeast extract, 5 g/L sodium chloride, 1 g/L sodium nitrate, 15 g/L glycerol, 20 g/L MOPS was used for production of Stambomycins. The pH was adjusted to 7.4 with 10M sodium hydroxide and 15 g/L of agar was added prior to auto-claving.

Twenty 10 cm×10 cm square Petri dishes each containing 50 mL of medium were used. A sterile cellophane membrane was placed on the agar in each plate and 20 µl of *Streptomyces ambofaciences* ATCC23877/OE484 spores from the stock were spread on top of each cellophane membrane. The plates were incubated for 4 days at 30° C. and the cellophane membranes were lifted off the plates. The mycelia were scraped off the cellophane membranes and combined. The mycelia were extracted with 3×200 mL of methanol. The combined extracts were concentrated to 200 mL under reduced pressure and passed through a 0.2 micron filter.

2. Purification of Stambomycins A, B, C and D

Stambomycins were partially purified from the concentrated methanol extract using semi-preparative HPLC on a reverse phase column (C18, 100×21 mm, fitted with C18 pre-column 10×21 mm). The mobile phases used were water (A) and acetonitrile (B), both with 0.1% formic acid added. The gradient employed was as follows: 0 minutes, 80% A/20% B; 10 minutes, 80% A/20% B; 20 minutes, 100% B; 35 minutes 100% B. Absorbance was monitored at a wavelength of 240 nm. Fractions containing Stambomycins were identified using ESI-MS and combined. The combined fractions were evaporated under reduced pressure and re-suspended in small volume of 50% aqueous methanol. Stambomycins were purified from the combined fractions by semi-preparative HPLC on the same column using the following gradient: 0 minutes, 60% A/40% B; 15 minutes, 5% A/95% B; 20 minutes, 100% B; 25 minutes, 100% B. Fractions containing a mixture of Stambomycins A and B were collected, combined and lyophilised as were separate fractions containing a mixture of Stambomycins C and D. 15.6 mg of Stambomycins A/B and 8.6 mg of Stambomycins C/D were obtained from twenty agar plates.

Figure 6:
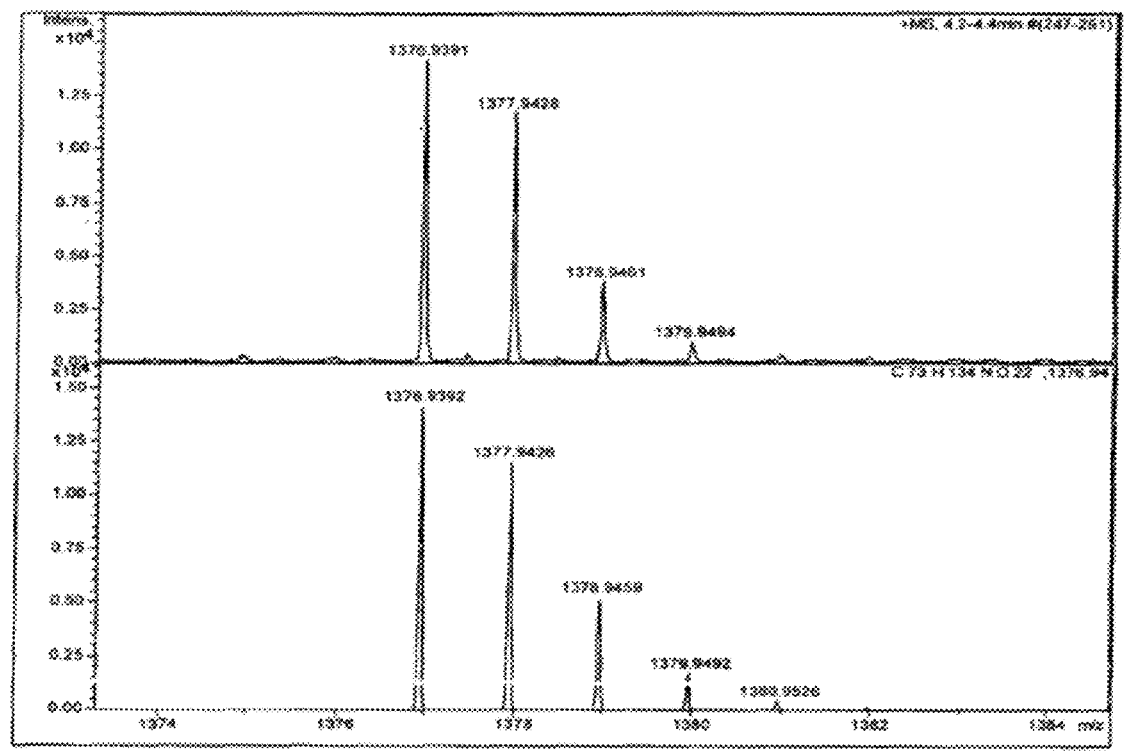
FIG. 6 represents the ESI-TOF mass spectrum of Stambomycins A/B (top) and the simulated mass spectrum for the $C_{73}H_{134}NO_{22}+$ ion (bottom).
Figure 7:
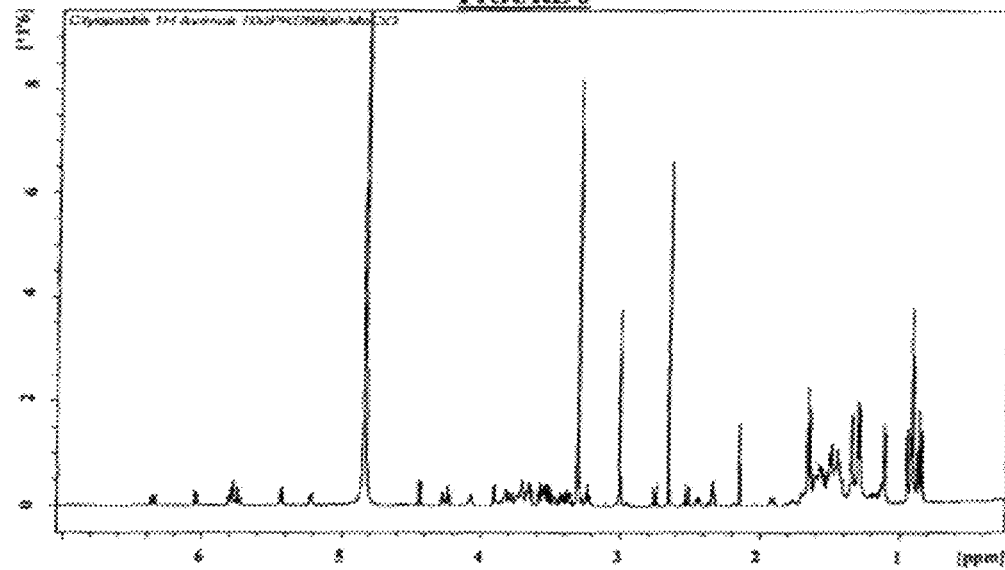
FIG. 7 represents the $^1$H-NMR spectrum (700 MHz) of Stambomycins A/B in $d_4$-MeOH.
Figure 8:
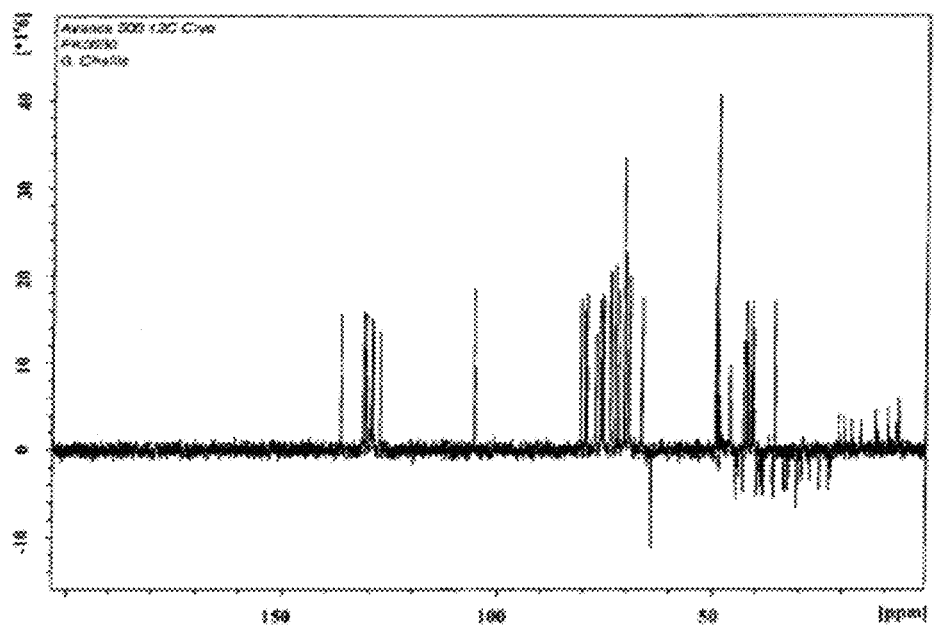
FIG. 8 represents the $^{13}$C-NMR spectrum (125 MHz) of Stambomycins A/B in $d_4$-MeOH.
Figure 9:
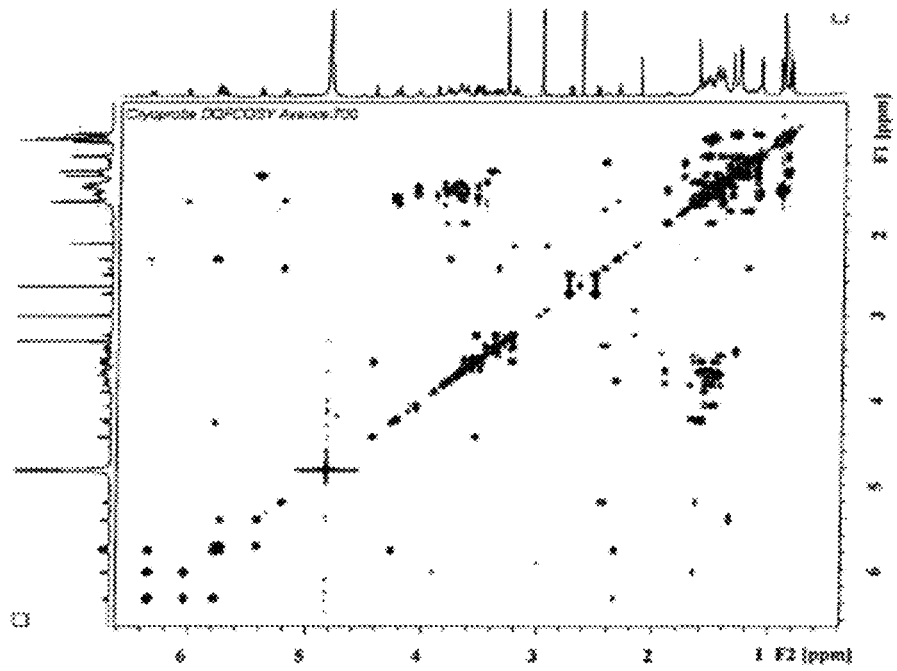
FIG. 9 represents the DQF-COSY spectrum (700 MHz) of Stambomycins A/B, in $d_4$-MeOH.
Figure 10:
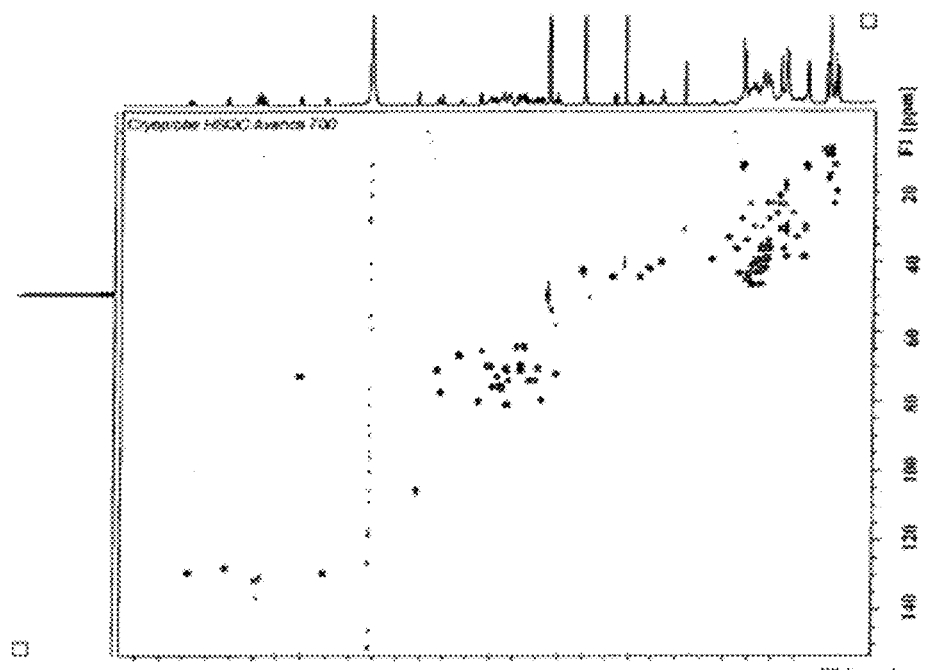
FIG. 10 represents the HSQC spectrum (700/175 MHz) of Stambomycins A/B in $d_4$-MeOH.
Figure 11:
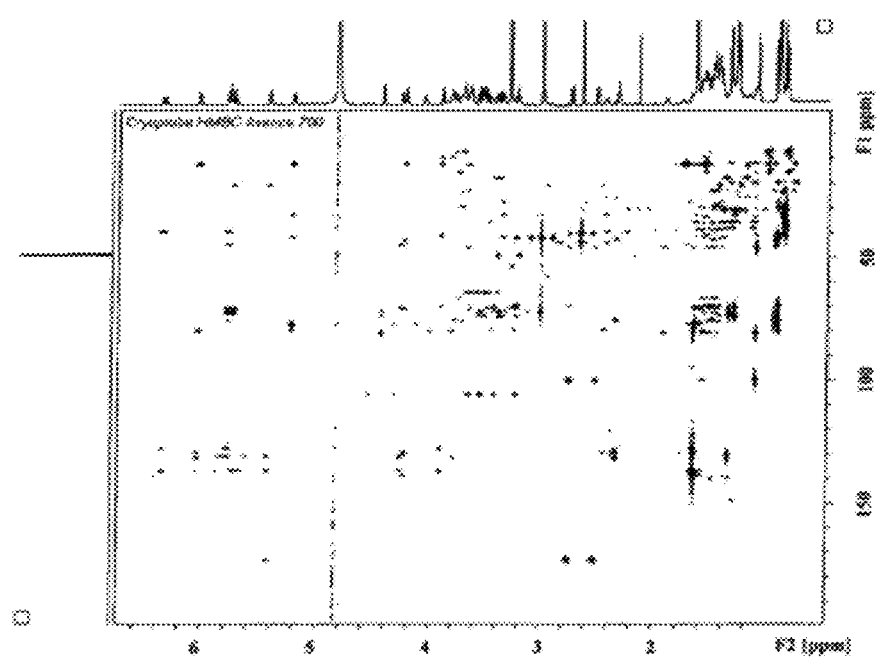
FIG. 11 represents the HMBC spectrum (700/175 MHz) of Stambomycins A/B in $d_4$-MeOH.
Figure 12:
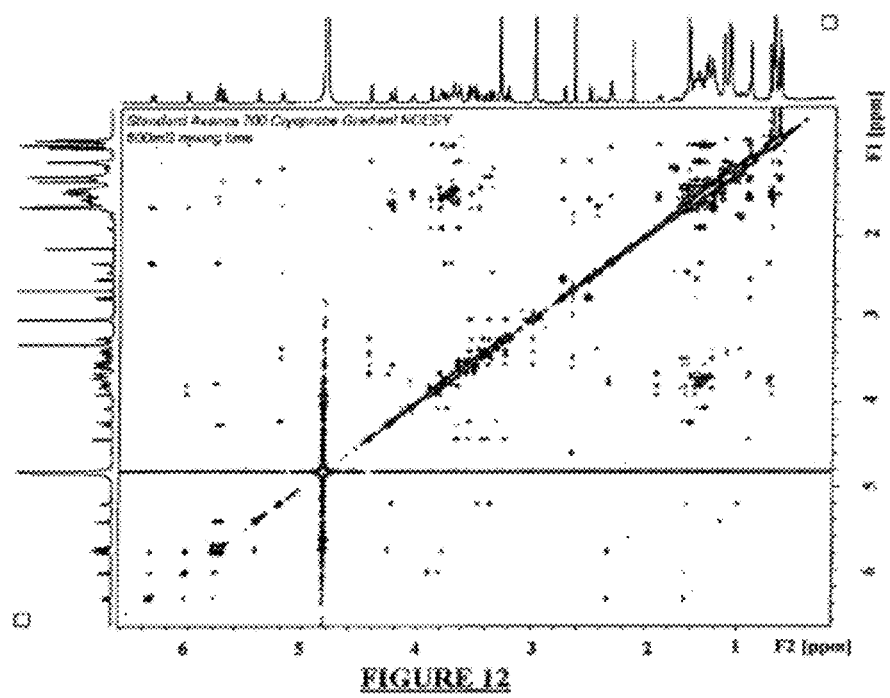
FIG. 12 represents the NOESY spectrum (700 MHz) of Stambomycins A/B in $d_4$-MeOH.
Figure 13:
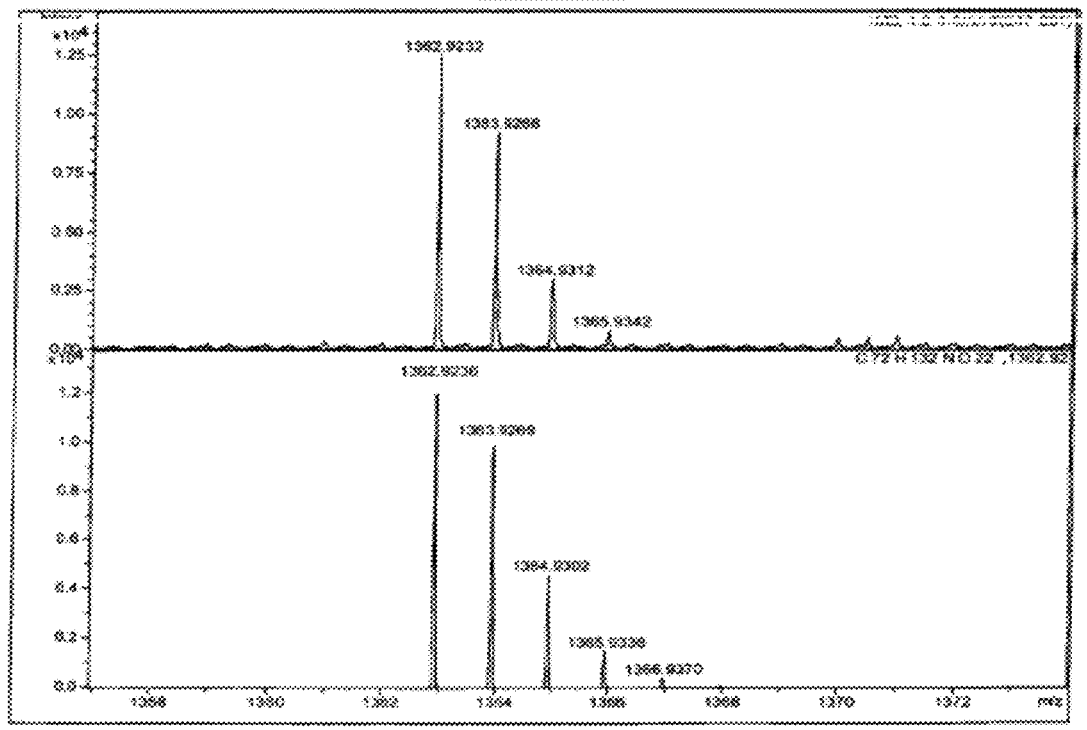
FIG. 13 represents the ESI-TOF mass spectrum of Stambomycins C/D (top) and the simulated mass spectrum for the $C_{72}H_{132}NO_{22}^+$ ion (bottom).
Figure 14:
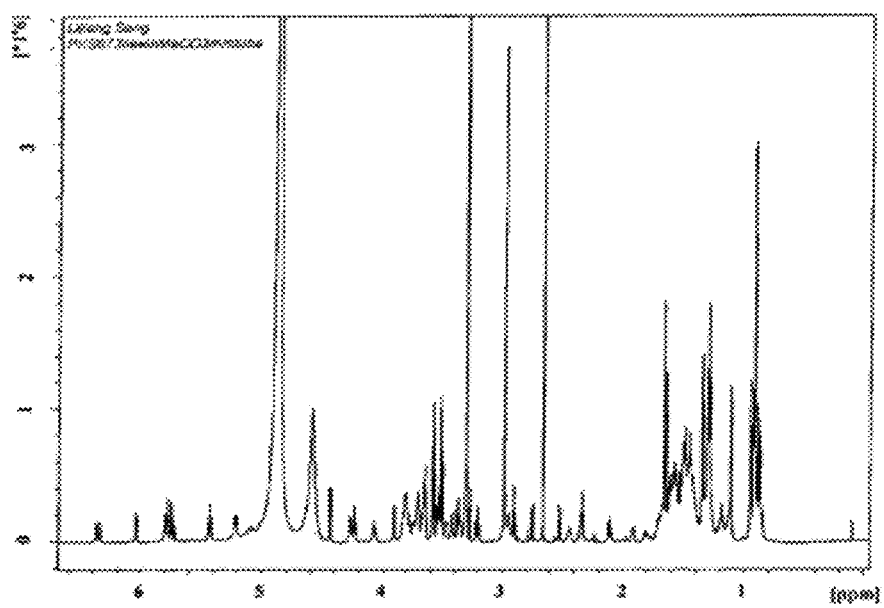
FIG. 14 represents the $^1$H-NMR spectrum (700 MHz) of Stambomycins C/D in $d_4$-MeOH.
Figure 15:
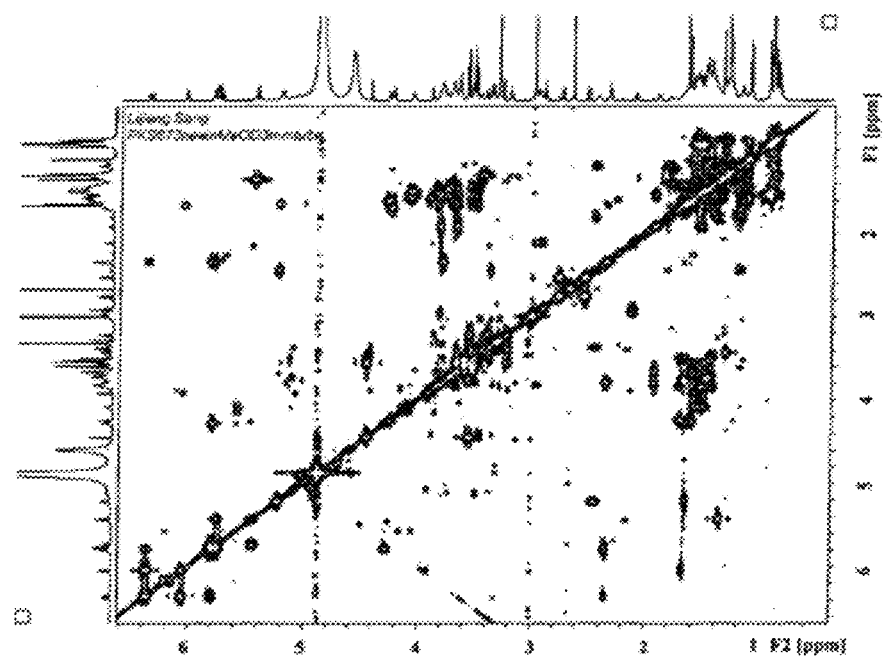
FIG. 15 represents the DQF-COSY spectrum (700 MHz) of Stambomycins C/D, in $d_4$-MeOH.
Figure 16:
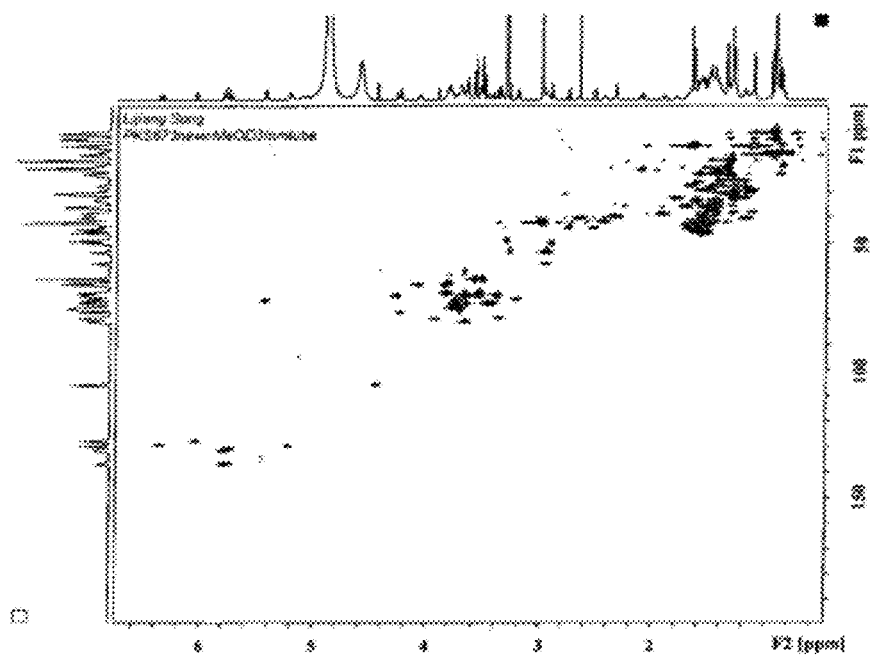
FIG. 16 represents the HSQC spectrum (700/175 MHz) of Stambomycins C/D in $d_4$-MeOH.
Figure 17:
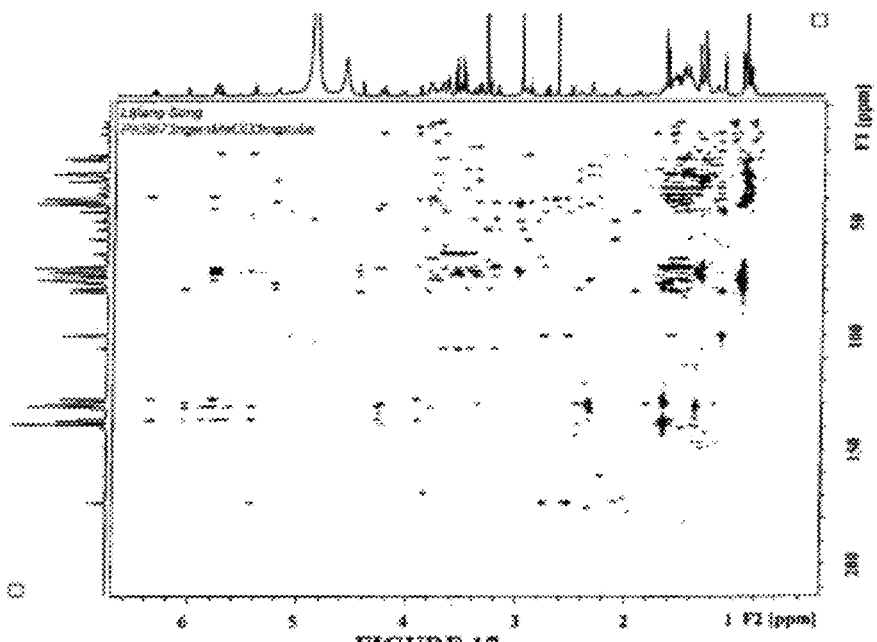
FIG. 17 represents the HMBC spectrum (700/175 MHz) of Stambomycins C/D in $d_4$-MeOH.
Figure 18:
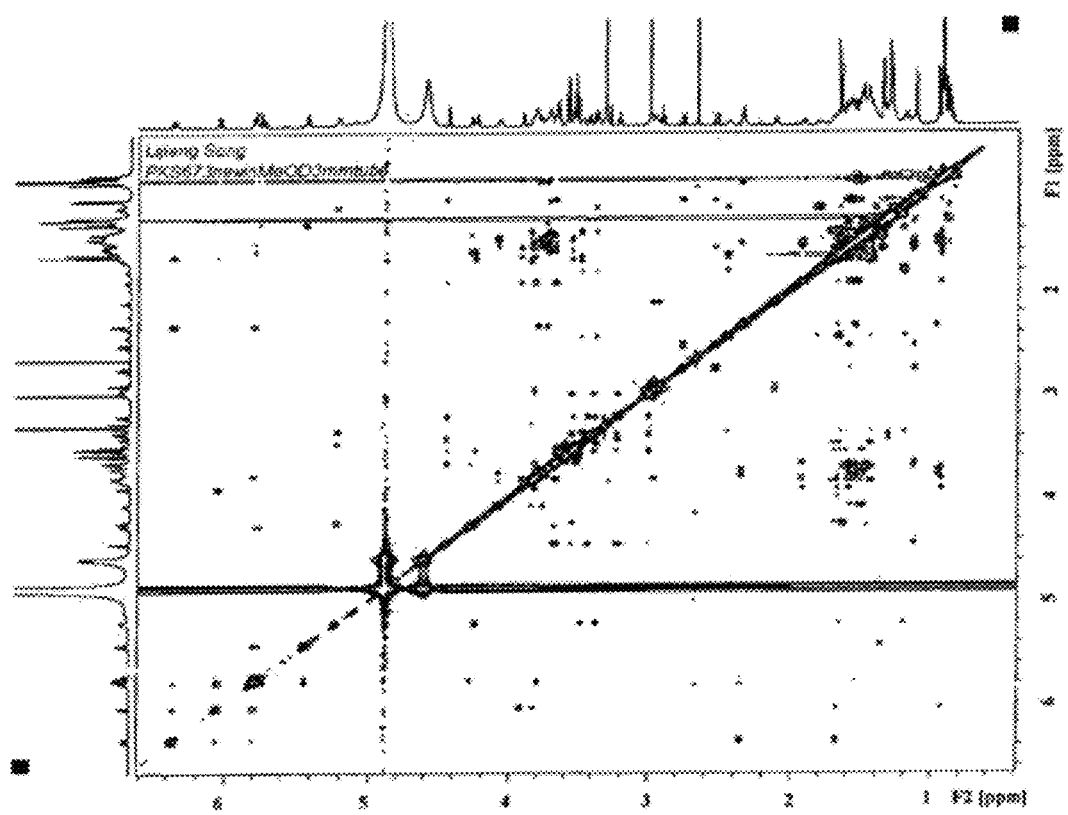
FIG. 18 represents the NOESY spectrum (700 MHz) of Stambomycins C/D in $d_4$-MeOH.
Figure 19:
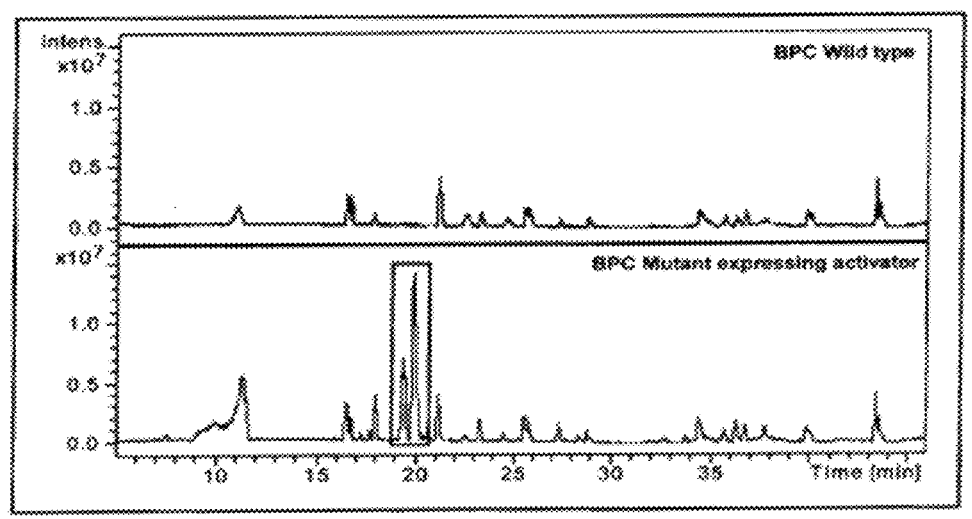
FIG. 19 represents the LC-MS base peak chromatogram for extracts from the control strain ATCC/pIB139 (top) and the mutant strain ATCC/OE484 (bottom). The two framed peaks, with retention times of approximately 19 and 20 min, correspond to Stambomycins C/D and A/B, respectively.

3. Structure Elucidation of Stambomycins A/B and C/D by NMR Spectroscopy and Mass Spectrometry High resolution ESI-TOF-MS analyses of Stambomycins A/B and C/D established their molecular formulae as $C_{73}H_{134}NO_{22}$ (Stambomycins A/B) and $C_{72}H_{132}NO_{22}$ (Stambomycins C/D) ([M+H]$^+$ calculated for $C_{73}H_{134}NO_{22}$: 1376.9392, found: 1376.9391; [M+H]$^+$ calculated for $C_{72}H_{132}NO_{22}$: 1362.9236, found: 1362.9232) (FIGS. 6 and 13 respectively).

Figure 20:
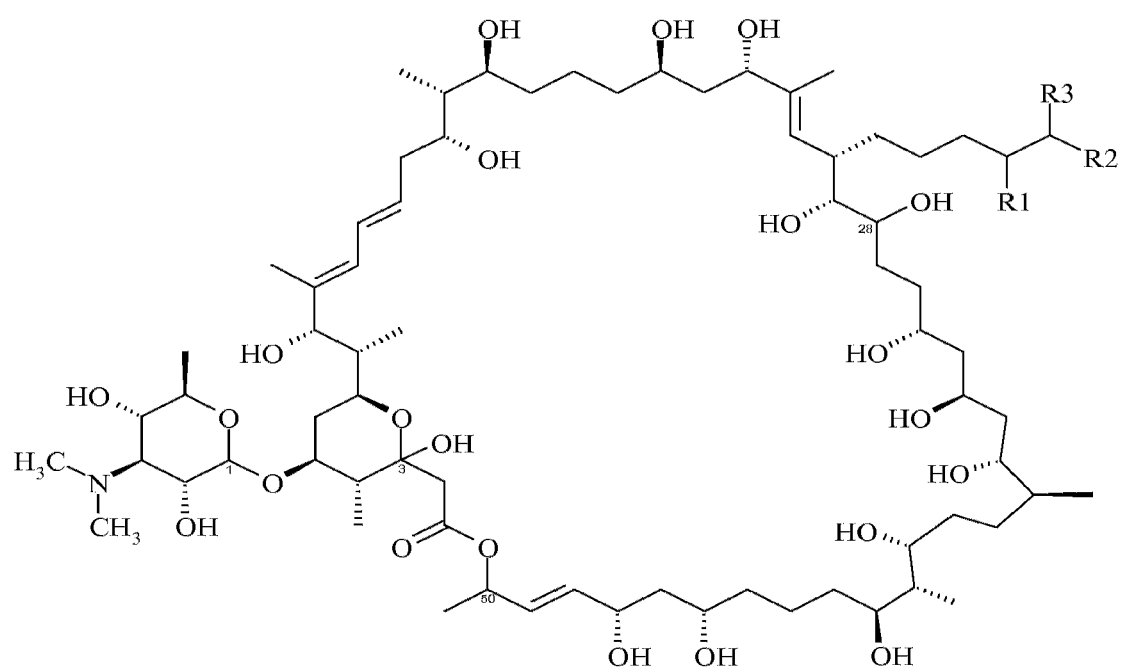
FIG. 20 represents the proposed structures of Stambomycins A, B, C and D elucidated by mass spectrometry, NMR spectroscopy and bioinformatics analyses. Carbons 1', 3, 28 and 50 are indicated on the structure.

$^1$H, $^{13}$C, COSY, NOESY, TOCSY, HSQC and HMBC NMR spectra (in $d_4$-MeOH and $d_6$-DMSO, FIGS. 7-12, 14-18) established the planar structures of Stambomycins A, B, C and D (FIG. 20). The absolute stereochemistry of the stereocentres in the macrolide ring of Stambomycins A, B, C and D was predicted by bioinformatics analyses using the method of (Keatinge-Clay et al. 2007, Kwan, David H et al. 2008). The stereochemistry at C-3, C-28 and C-50, as well as the R$^1$ group in the C-26 alkyl chain, could not be predicted using these analyses. The absolute stereochemistry of the stereocentres in the mycaminose residue of Stambomycins A, B, C and D was predicted using bioinformatics analyses based on the known pathway for TDP-D-mycaminose biosynthesis from D-glucose-1-phosphate (*Melancon*, Charles. et al. 2005). The stereochemistry of C-1' could not be predicted using these analyses.

4. The production of Stambomycins A/B and C/D with *Streptomyces ambofaciens* DSM 40697 and ATCC15154 strains transformed with LAL transcription factor, according to the procedure defined above was also analysed in liquid R2 medium.

Example 4

Antimicrobial Effects of Stambomycins

The antibacterial properties of mixtures of Stambomycins A/B (M2) and Stambomycins C/D (M1) have been tested.

1—First, the antibacterial effects of M1 and M2 have been tested on LB soft agar plates, using Gram-positive *Bacillus subtilis* ATCC 6633 and *Micrococcus luteus* as indicator strains.

The mixtures were added directly on the surface of the medium.

The plates were incubated at 4° C. for two hours to allow diffusion of the antibiotic and then at 30° C. (for *B. subtilis*) or 37° C. (for *M. luteus*) over night.

M1 and M2 were diluted with $H_2O$, and added at the following dosages: M1: 1 µg, 3 µg, 5 µg, and 10 µg; M2: 1.25 µg, 2.5 µg, 10 µg and 12.5 µg.

Figure 21A:
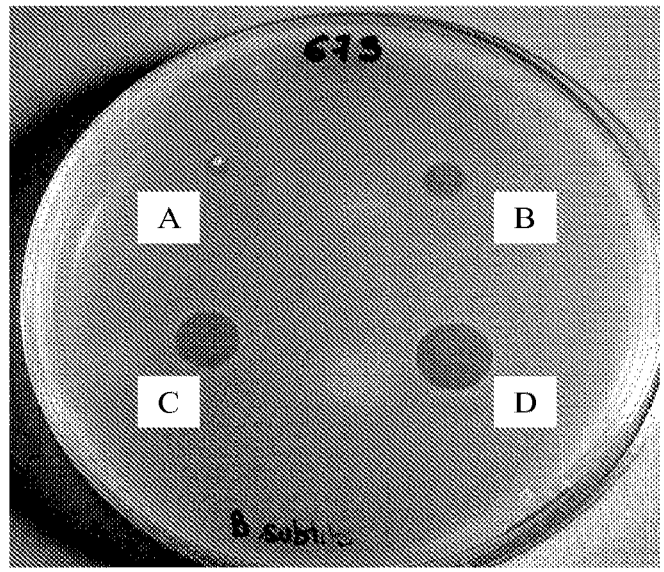
FIGS. 21A-B represents the effects of Stambomycin A/B and C/D on *Bacillus subtilis* proliferation.
Figure 21B:
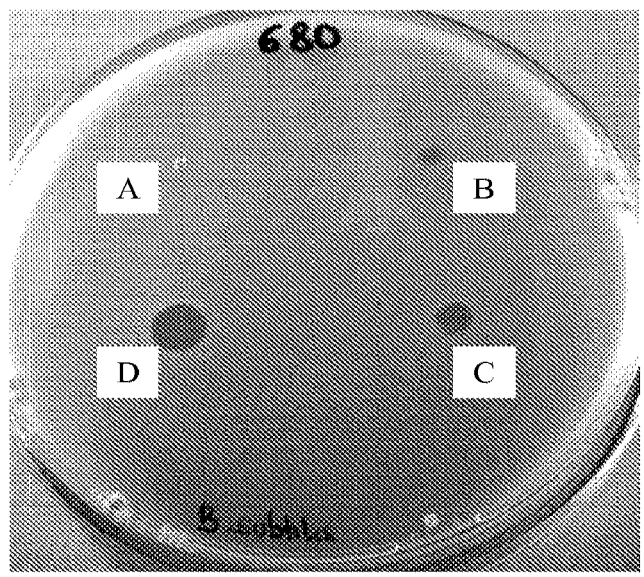
Figure 22A:
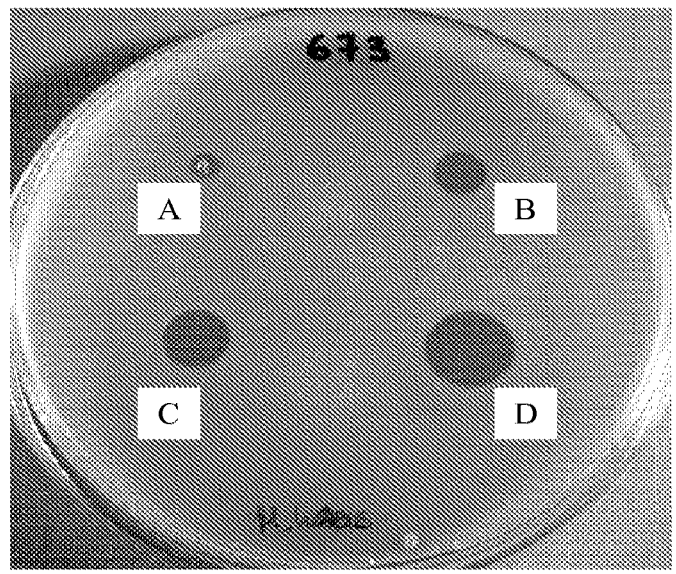
FIGS. 22A-B represents the Stambomycins A/B and C/D effects on *Micrococcus luteus* proliferation
Figure 22B:
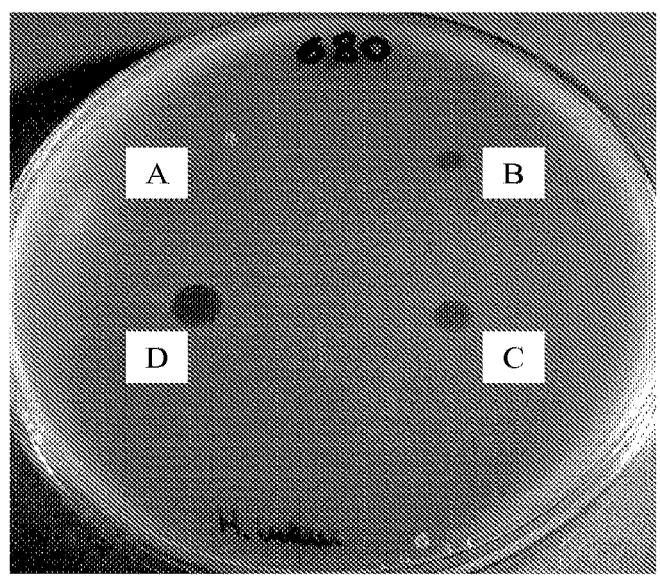
Figure 23:
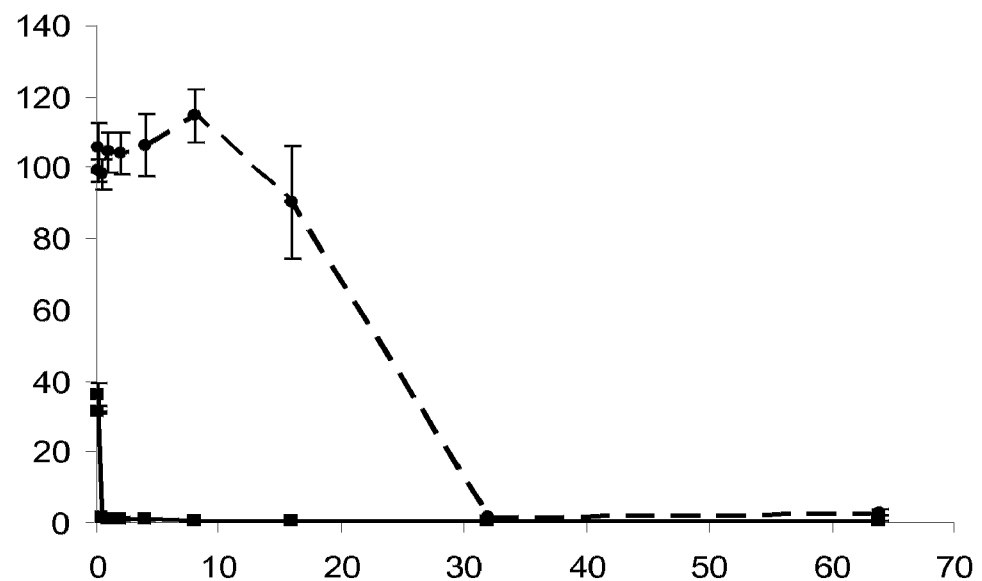
FIG. 23 represents a *Bacillus subtilis* proliferation curve in the presence of Vancomycin or Stambomycin C/D. The Y-axis represents relative proliferation in % compared to *B. subtilis* cultured without drug, and the X-axis represents the drug concentration in µg/mL. The solid line represents the dose response curve with Vancomycin, and the hashed line represents the dose response curve with Stambomycins C/D.
Figure 24:
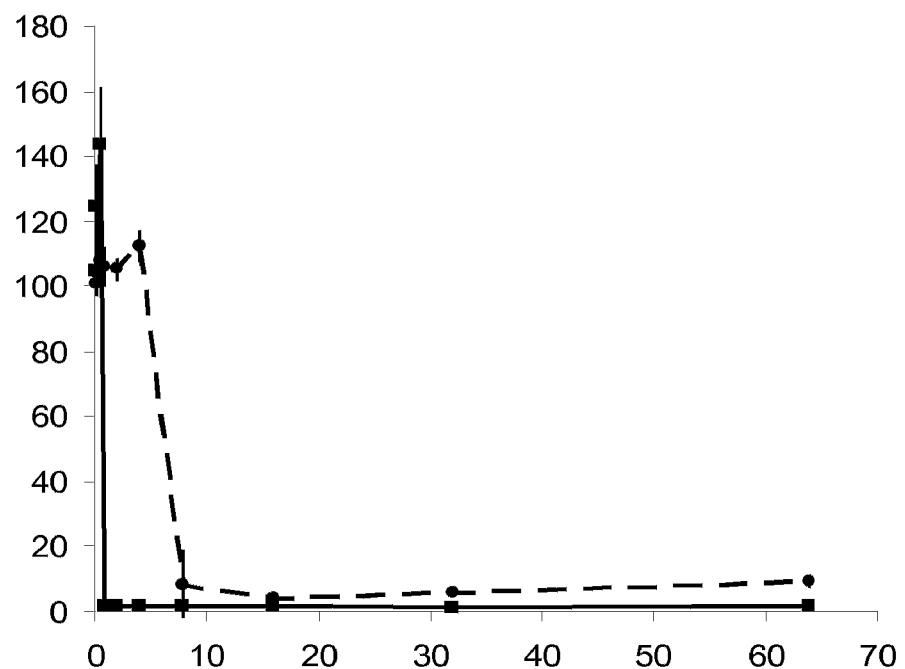
FIG. 24 represents the *Enterococcus faecalis* proliferation curve in the presence of Vancomycin or Stambomycins C/D. The Y-axis represents relative proliferation in % compared to *E. faecalis* cultured without drug, and the X-axis represents the drug concentration in µg/mL. The solid line represents the dose response curve with Vancomycin, and the hashed line represents the dose response curve with Stambomycins C/D.
Figure 25:
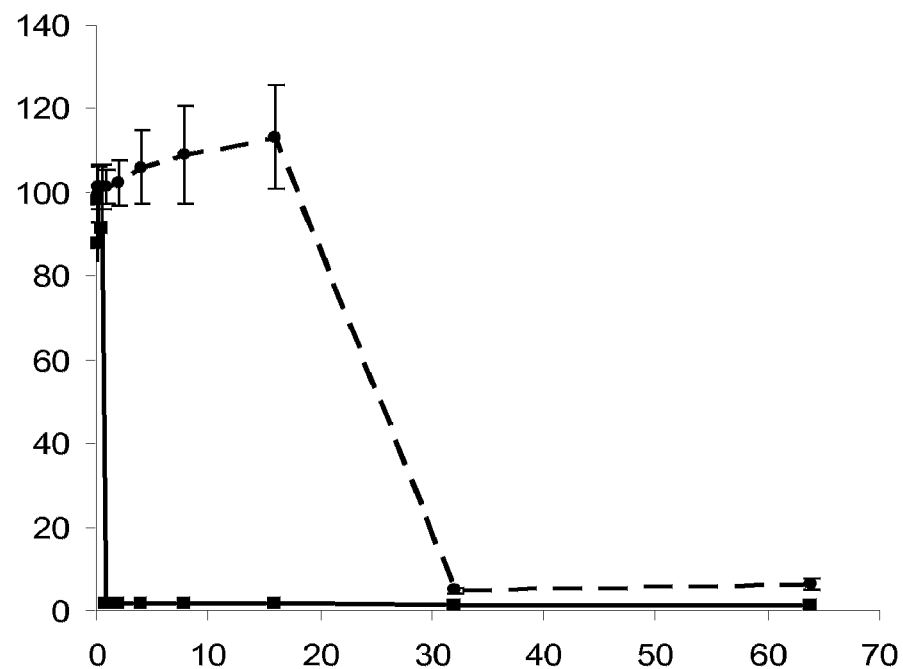
FIG. 25 represents the *Staphylococcus aureus* proliferation curve in the presence of Vancomycin or Stambomycins C/D. The Y-axis represents relative proliferation in % compared to *S. aureus* cultured without drug, and the X-axis represents the drug concentration in µg/mL. The solid line represents the dose response curve with Vancomycin, and the hashed line represents the dose response curve with Stambomycins C/D.
Figure 26:
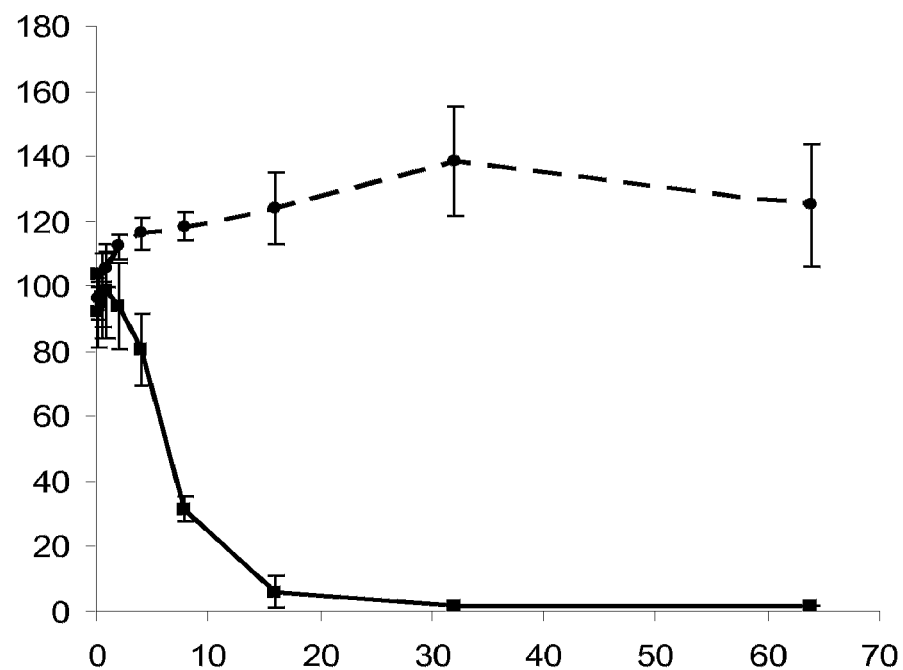
FIG. 26 represents the *Mycobacterium smegmatis* proliferation curve in the presence of Kanamycin or Stambomycins C/D. The Y-axis represents relative proliferation in % compared to *M. smegmatis* cultured without drug, and the X-axis represents the drug concentration in µg/mL. The solid line represents the dose response curve with Kanamycin, and the hashed line represents the dose response curve with Stambomycins C/D.

The results for *B. subtilis* are shown in FIGS. 21A and 21B, and the results for *M. luteus* are shown in FIGS. 22A and 22B.

As shown in FIGS. 21 and 22, strains turned out to be susceptible to both the molecules when 1 µg is used. However, Stambomycins C/D appear to be more active than Stambomycins A/B.

2—Second, the antibacterial effects of M1 and M2 have been tested by determining 90% inhibiting concentration ($IC_{90}$) on proliferation of *B. subitilis, Enterococcus faecalis, Staphylococcus aureus* and *Mycobacterium smegmatis*.

Bacteria were inoculated at 10$^6$ cells/mL in LB (Luria Bertani) medium, except for *E. faecalis* which was inoculated in Muller Hinton (MH) medium, in the presence of M1 or M2 at a concentration varying from about 0.14 µg/mL to about 70 µg/mL. After 24 h, the number of cells was counted.

Proliferation of the above mentioned bacteria in the presence of M1 or M2 was compared to the proliferation of said bacteria in the presence of Vancomycin, (or Kanamycin for *Mycobacterium smegmatis*)

The results for M1 are represented in FIGS. 23 to 26.

As seen in the figures, M1 inhibits growth of the bacteria tested, except *M. smegmatis*.

The calculated $IC_{90}$ values are presented in table 3.

TABLE 3

| $IC_{90}$ values for Stambomycins | |
|---|---|
| Strain | M1 $IC_{90}$ |
| *B. subtilis* | 33.53 +/− 0.86 µg/mL corresponding to 25.29 +/− 0.65 µM |
| *E. faecalis* | 8.65 +/− 0.49 µg/mL corresponding to 6.52 +/− 0.37 µM |
| *S. aureus* | 33.95 +/− 0.16 µg/mL corresponding to 25.6 +/− 0.12 µM |

Similar results were obtained with the M2 mixture.

3—The anti fungal properties of M1 and M2 have been also evaluated.

4—The anti parasitic properties of M1 and M2 have been also evaluated.

5—Finally, the anti viral properties of M1 and M2 have been also evaluated.

Example 5

Antiproliferative Effects of Stambomycins

Cytotoxicity was tested using CHO-K1 cells and anti-proliferative activity was examined using HT29 cells.

The effects were compared with Doxorubicin and Sodium butyrate.

Both M1 and M2 are less cytotoxic than Doxorubicin (Table 4) and, more importantly, they revealed an interesting activity on the tumour cell line HT29 from a human colon adenocarcinoma (Table 4).

TABLE 4 represents the cytotoxicity and antitumor assays of both M1 and M2.

| Compounds | IC50 (µM) for CHO-K1 | IC50 (µM) for HT29 |
|---|---|---|
| Doxorubicin | 1.99 +/− 0.25 | 1.32 +/− 0.08 |
| Sodium butyrate | | 4890 +/− 72 |
| M1 | 8.46 +/− 0.52 | 1.77 +/− 0.04 |
| M2 | 8.47 +/− 0.67 | 1.74 +/− 0.04 |

CHO-K1 is an ovary sane cell line from an adult Chinese hamster. HT29 is a tumour cell line from a human colon adenocarcinoma. Doxorubicin and sodium butyrate are controls.

Similar results were obtained with other tumorigenic cells lines: MCF-7 human breast cancer cell line, PC-3 human prostate cancer cell line, and H460 human lung cancer cell line. Also, cells lines such as HL-60 and K562 have been tested.

The following table 5 represents the cytotoxicity and antitumor assays of both M1 and M2, in H460, MCF7 and PC3 cell lines.

| Compounds | IC50 (µM) for H460 | IC50 (µM) for MCF7 | IC50 (µM) for PC3 |
|---|---|---|---|
| M1 | 1.3 +/− 0.13 | 3.51 +/− 0.16 | 2.79 +/− 0.18 |
| M2 | 1.49 +/− 0.03 | nd | 3.39 +/− 0.16 | nd: not determined

Example 6

Activation of the Silent Modular Polyketide Synthase Gene Cluster in *Streptomyces ambofaciens*, by Culturing in R2 Medium Composition of R2 medium is disclosed in Example 1.

The production of Stambomycins by the wild-type strain *Streptomyces ambofaciens* ATCC23877 was analysed in R2 medium. This medium is not usually used for production of macrolides and was not expected to be suitable for the production of Stambomycins.

The strain was grown in R2 medium and the supernatant and mycelium were extracted with ethyl acetate. The protocol is the same as the one used for the extraction of the ATCC/OE484 strain grown on MP5 medium.

The extracts were analysed using Liquid-Chromatography Mass Spectroscopy (LC-MS). As control, extracts from:
 ATCC/OE484 strain grown in R2 medium
 ATCC/OE484 strain in which the SAMR0467 ORF has been deleted, grown in R2 medium,
 ATCC 23877 strain in which the SAMR0467 ORF has been deleted, grown in R2 medium, and
 ATCC 23877 strain in which the SAMR0484 ORF, grown in R2 medium
were also were analysed using LC-MS.

Results are shown in FIGS. 27 to 32.

Unexpectedly, the LC-MS base peak chromatogram of the mycelium extract revealed two peaks, giving doubly charged ions with m/z of 680 and of 673 (positive ion mode) corresponding to molecular formulae:
 $C_{73}H_{134}NO_{22}$ (Stambomycins A/B) (FIGS. 27B, 28 and 31E).
 $C_{72}H_{132}NO_{22}$ (Stambomycin C/D) (FIGS. 29B, 30 and 32E).

These peaks are similar to those obtained with the ATCC/OE484 strain cultured as disclosed in Example 2 (FIGS. 27A, 31D, 29A and 32D).

The peaks were not present in the mycelium extract of the wild type strain deleted for SAMR0467 (FIGS. 31A and 32A), which encodes the first PKS involved in the biosynthesis of the Stambomycins, and the mycelium extract of the wild type strain deleted for SAMR0484 (FIGS. 31B and 32B), nor in the mycelium extract of the ATCC/OE 484 strain deleted for SAMR0467 (FIGS. 31C and 32C), when grown in the same conditions as the wild-type strain (i.e. in R2 medium).

These data confirmed that the peak observed in the wild-type strain is due to the Stambomycins.

The production of Stambomycins in R2 by the wild-type strain is explained by the fact that the expression of the biosynthetic genes is activated in this growth condition.

The production of Stambomycins A/B and C/D by the wild-type strain *Streptomyces ambofaciens* DSM 40697 and ATCC15154 was also analysed in liquid R2 medium.

The invention claimed is:

1. A compound selected from the group consisting of:

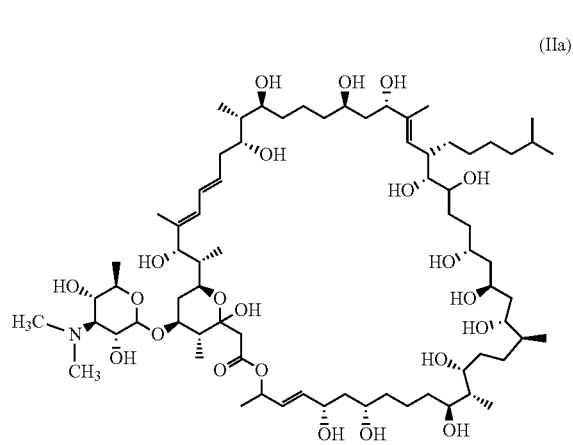
(IIa)

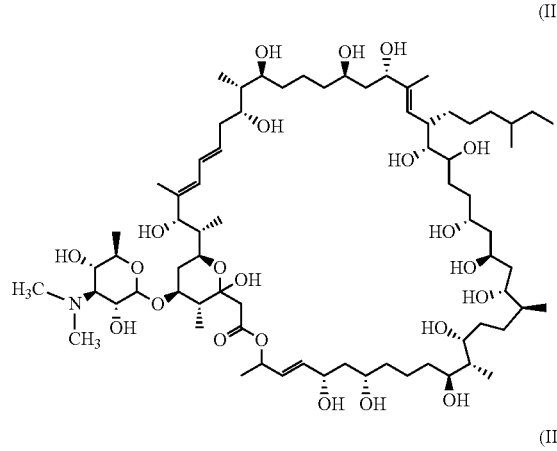
(IIb)

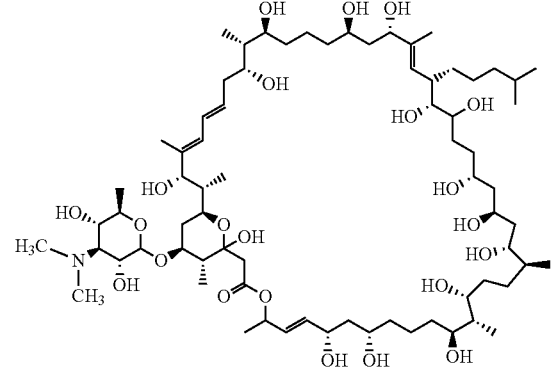
(IIc)

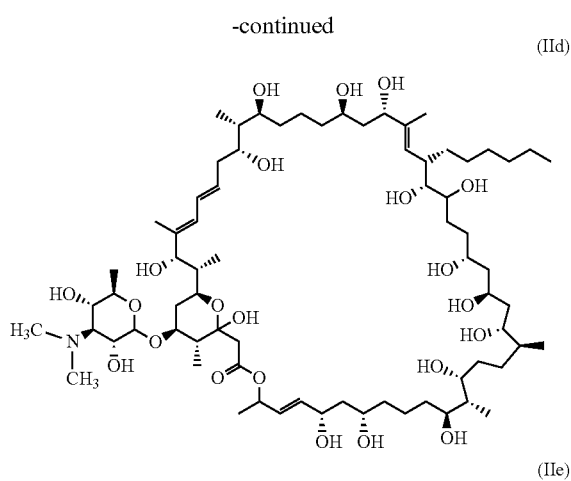
(IId)

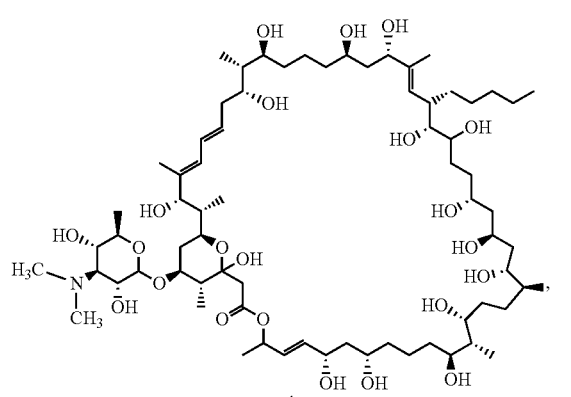
(IIe)

and

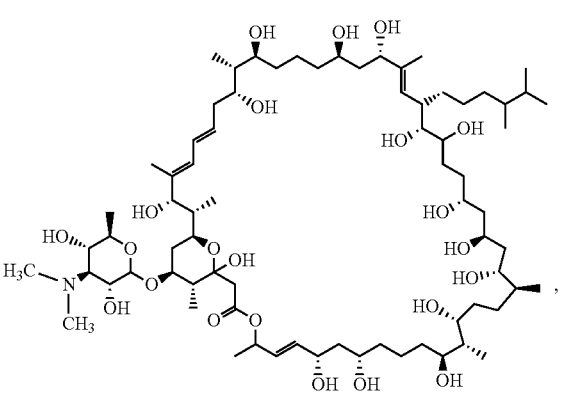
(IIf)

said compound being in the form of a racemate, any one of its enantiomers or diastereomers, or any one of the tautomers of said racemates, enantiomers and diastereomers, or a respective pharmaceutically acceptable salt thereof.

2. A process for producing the compound of claim 1, comprising:

activating a silenced large type I polyketide synthase (PKS) gene cluster of a microorganism belonging to the family of Streptomycetaceae, either by artificially over-expressing a transcriptional activator in said microorganism, wherein said transcriptional activator comprises the amino acid sequence SEQ ID NO: 1, or by culturing said microorganism in R2 medium allowing the expression of said transcriptional activator at a level sufficient to activate the expression of said PKS genes, said microorganism being *Streptomyces ambofaciens* deposited at the American Type Culture Collection (ATCC) under the number ATCC 23877; and isolating said compound.

3. An isolated microorganism producing the compound of claim 1, said microorganism being deposited at the Collection Nationale de Culture des Microorganismes (CNCM; Institut Pasteur), under the number CNCM-I-4175, said microorganism being transformed to permanently express a transcriptional activator consisting of the amino acid sequence SEQ ID NO: 1.

4. A pharmaceutical composition, comprising at least one compound according to claim 1 as active ingredient, in association with a pharmaceutically acceptable vehicle.

5. A method for treating pathologies associated with a bacterial infection, comprising administering to an individual in need thereof an effective amount of at least one compound as defined in claim 1.

6. A method for treating cancer, comprising administering to an individual in need thereof an effective amount of at least one compound as defined in claim 1.

7. The process according to claim 2, wherein said PKS gene cluster is located about 500 Kbases from the end of the right arm of the chromosome of said microorganism.

8. The pharmaceutical composition according to claim 4, further comprising at least one additional antitumor compound or at least one additional antibacterial compound.

9. The method according to claim 5, wherein the effective amount of the at least one compound is from about 2 to 5 g/day.

10. The method according to claim 5, wherein the effective amount of the at least one compound is from about 50-100 mg/kg/day.

11. The method according to claim 5, wherein the pathology associated with a bacterial infection is sepsis, septicemia, nosocomial disease, *Staphylococcus aureus* infection, Lyme disease, cellulitis, osteomylitis, syphilis, bacterial meningitis or plague.

12. The method according to claim 5, wherein the cancer is lung cancer, breast cancer, prostate cancer, bladder cancer, intestinal cancer, colon cancer, skin cancer, brain cancer, leukemia or lymphoma.

* * * * *

UNITED STATES PATENT AND TRADEMARK OFFICE
CERTIFICATE OF CORRECTION

PATENT NO.        : 8,664,186 B2                                          Page 1 of 1
APPLICATION NO.   : 13/378954
DATED             : March 4, 2014
INVENTOR(S)       : Aigle et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 57 days.

Signed and Sealed this

Twenty-ninth Day of September, 2015

Michelle K. Lee
*Director of the United States Patent and Trademark Office*

SEQUENCE LISTING

```
<160> NUMBER OF SEQ ID NOS: 18

<210> SEQ ID NO 1
<211> LENGTH: 958
<212> TYPE: PRT
<213> ORGANISM: Streptomyces ambofaciens

<400> SEQUENCE: 1

Met Leu Val His Arg Asp Glu Gln Leu Ala His Leu Arg Trp Ala Phe
1               5                   10                  15

His Ala Cys Glu Lys His Gly His Gly Gln Val Ala Leu Val Thr Gly
            20                  25                  30

Ala Val Gly Ser Gly Lys Thr Gln Val Leu Glu Thr Phe Gly Glu Trp
        35                  40                  45

Ala Ala Thr Ala Gly Gly Gln Val Leu Ser Ala Ala Gly Ser Arg Ala
    50                  55                  60
```

```
Glu Gln Gly Leu His Phe Gly Val Leu Gly Leu Leu His Ser Ala
 65                  70                  75                  80

Arg Leu Lys Pro Glu Gly Ile Arg Glu Val Glu Leu Ile Arg Glu
                 85                  90                  95

Val Ala Leu Ala Val Pro Thr Ala Glu Ala Arg Ser Gly Ala Ala Pro
            100                 105                 110

Glu Thr Leu Ala Glu Ala Leu Thr Ala Asp Gly Leu Trp Ala Pro Leu
            115                 120                 125

Leu Arg Thr Ala Phe Asp Thr Phe Leu Thr Leu Ala Gly Arg Gly Pro
            130                 135                 140

Leu Val Leu Ala Val Asp Asp Leu Gln His Thr Asp Ala Ala Ser Leu
145                 150                 155                 160

His Cys Leu Leu Tyr Val Thr Arg Arg Leu Arg Asn Ala Arg Ile Met
                165                 170                 175

Val Leu Leu Ser Glu Ala Thr Thr Leu Arg Pro Ala His Pro Leu Phe
            180                 185                 190

His Ala Glu Leu Arg Ser Leu Pro Arg Phe Thr Arg Val Thr Leu Pro
            195                 200                 205

Leu Leu Thr Ala Asp Ser Val Ser Arg Leu Leu Gly Glu Glu Ala Gly
            210                 215                 220

Thr Pro Asp Val Arg Gly Asp Gly Ala Gly Ala Pro Asp Val Arg Glu
225                 230                 235                 240

Glu Ala Gly Arg Ile Leu Arg Val Thr Gly Gly Asn Pro Leu Leu Ser
                245                 250                 255

Gln Ala Leu Val Asp Glu Arg Ala His Arg Gly Thr Asp Ser Ala Pro
            260                 265                 270

Asp Thr Gly Ala Arg Ala Gly Asp Thr Phe Glu Arg Ala Val Leu Asp
            275                 280                 285

Cys Leu Tyr Arg His Glu Pro Gly Val Arg Leu Val Ala Gln Ala Leu
            290                 295                 300

Ala Ala Leu Asp Arg Pro Ala Ser Pro Glu Leu Leu Gly Gln Leu Leu
305                 310                 315                 320

Asp Val Leu Pro Asp Ser Thr Val Pro Ala Val Arg Val Leu Glu Gly
                325                 330                 335

Ala Gly Leu Val His Ala Gly Arg Leu Arg His Pro Arg Ile Val Leu
            340                 345                 350

Ala Val Arg Ser Asp Met Pro Ala Glu Glu Arg Arg Leu His Gln
            355                 360                 365

Arg Ala Ala Glu Val Leu His Glu Asn Gly Ala Glu Ala Ser Val Val
            370                 375                 380

Ala Glu His Leu Val Ala Ser Ala Trp Thr Asp Gly Ala Trp Val Val
385                 390                 395                 400

Pro Val Leu Arg Asp Ala Ala His Ala Leu Ser Thr Gly Arg Pro
                405                 410                 415

Asp His Ala Ala Ala Cys Leu Arg Leu Gly Gly Arg Ala Glu Thr Asp
            420                 425                 430

Lys Asp Arg Arg Asn Ser Leu Met Ala Met Leu Ile Thr Ala Arg Trp
            435                 440                 445

Gln Val Asn Pro Leu Ala Val Thr Gly Gln Val Ser Gln Leu Val Glu
            450                 455                 460

Ala Ala Arg Ala Asp Glu Ser Ser Pro Ser Thr Ala Val Ser Ala Val
465                 470                 475                 480

Pro Tyr Leu Leu Trp Gln Gly Arg Ala Glu Glu Ala Ala Glu Ala Ile
```

```
                  485                 490                 495
Ser Gly Cys Gly Ala Gly Asp His Gly Pro Ala Ser Asn Glu Leu Arg
            500                 505                 510

Leu Thr Arg Leu Leu Ile Ala Leu Ser His Pro Asp Tyr Leu Gly Thr
        515                 520                 525

Val Arg Glu Asp Pro Ser Ser Trp Thr Arg Ala Ala Thr Ala Pro Asp
    530                 535                 540

Ser Ala Ser Pro Leu Leu Gln Ala Val Ser Val Leu Gly Asn Ala Leu
545                 550                 555                 560

Met Pro Thr Gly Gly Val Asp Thr Val Ala Ala Ala Glu Gln Leu Leu
            565                 570                 575

Glu Arg His His Thr Asp Ser Gly Ser Leu Gly Leu Leu Thr Ala Pro
        580                 585                 590

Leu Leu Ala Leu Leu Cys Ala Gly Pro Ala Asp Arg Val Ala Val Trp
    595                 600                 605

Gly Glu Arg Leu Leu Ala Arg Gln Gly Val Gln His Thr Pro Ala Trp
610                 615                 620

Arg Gly Val Ile Arg Ala Ile His Ala Glu Ala Thr Leu Arg Leu Gly
625                 630                 635                 640

Asp Met Asp Ala Ala Glu Arg Gly Ala Arg Leu Ala Leu Glu Asp Leu
            645                 650                 655

Pro Ala Pro Ala Trp Gly Val Ala Val Gly Gly Pro Leu Gly Thr Leu
        660                 665                 670

Ile Thr Cys Thr Thr Glu Ser Gly Arg Leu Phe Glu Ala Glu Arg Trp
    675                 680                 685

Leu Ser Gln Pro Val Pro Ala Gly Val Phe Arg Thr Pro Val Gly Ala
690                 695                 700

His Tyr Leu Ile Ala Arg Gly Arg His His Leu Ala Met Gly Gln His
705                 710                 715                 720

Gln Ala Ala Ala Ala Asp Leu His Arg Ser Gly Glu Leu Val Arg Ser
            725                 730                 735

Trp Gly Ile Asp Val Ala Gly Leu Val Pro Trp Arg Leu Glu Leu Ala
        740                 745                 750

Arg Val Gln Leu Ser Leu Gly His Arg Thr His Ala Ala Gln Leu Leu
    755                 760                 765

Gln Glu Gln Leu Gln Val Ser Arg Gly Leu Asp Asp Arg Thr Arg Gly
770                 775                 780

Arg Ala Leu Arg Leu Leu Ala Ser Thr Ala Thr Pro Val Leu Arg Arg
785                 790                 795                 800

Lys Leu Leu Ser Lys Ala Val Thr Val Leu Gln Ala Cys Ser Asp Gln
            805                 810                 815

Gln Glu Leu Ala Arg Ala Leu Ser Asp Thr Ser Gln Thr Leu Pro Gln
        820                 825                 830

Thr Gly Asp Ala Pro Arg Ala Arg Leu Phe Val Arg Ala Gly Arg
    835                 840                 845

Leu Ala Gln Ala Ser Gly Arg Ala Pro Ala Leu Pro Gln Gln Val Gln
850                 855                 860

Arg Arg Ser Ala Pro Ser Asp Ala Ala Pro Thr Gly Ser Ser Ser
865                 870                 875                 880

Asp Ala Ser Ser Asp Gly Phe Glu Ser Arg Asp Gln Asp Gly Leu Leu
            885                 890                 895

Ser Glu Ala Glu Arg Arg Val Ala Val Leu Ala Ala Arg Gly Arg Thr
        900                 905                 910
```

```
Asn Arg Gln Ile Ser Asn Glu Leu Tyr Ile Thr Val Ser Thr Val Glu
        915                 920                 925

Gln His Leu Thr Arg Val Tyr Arg Lys Leu Asp Val Lys Ser Arg Thr
    930                 935                 940

Asp Leu Pro Asn Arg Leu Met Ala Leu Ala Glu Pro Met Ala
945                 950                 955

<210> SEQ ID NO 2
<211> LENGTH: 2877
<212> TYPE: DNA
<213> ORGANISM: Streptomyces ambofaciens

<400> SEQUENCE: 2
```

| | | | | | |
|---|---|---|---|---|---|
| atgctggtcc | atcgagacga | acaactggcc | catctacgct | gggcgttcca | cgcctgtgag   60 |
| aagcacggac | acggacaggt | ggcgctggtc | accggcgctg | tgggcagcgg | taagacccag  120 |
| gtgctggaga | ccttcgggga | gtgggctgcc | accgccggtg | ggcaggtgct | gagcgccgcc  180 |
| gggtcacgcg | ccgagcaggg | actccatttc | ggagtgctcg | gcaactcctg | cacagcgcg   240 |
| cggctcaaac | cggaggggat | ccgggaggtc | gaggagctga | tacgcgaggt | cgcgctggcg  300 |
| gtgcccacgc | ggaggcccg  | aagcggcgcg | cgcccgaga  | ccttagccga | ggccctgaca  360 |
| gcggacgggc | tctgggcgcc | actgctgcgg | accgccttcg | acacgttcct | gaccctggcc  420 |
| ggccgagggc | ctctggtgct | ggcggtcgac | gacctccagc | acacggacgc | cgcctcactg  480 |
| cactgtctgc | tctacgtcac | ccgaagactc | agaaacgcac | gcatcatggt | gctgctctcg  540 |
| gaggcgacga | cgctgcgtcc | ggcgcatccg | ctcttccacg | cggagctgcg | cagcctgcct  600 |
| cgcttcaccc | gggtcaccct | gccgctcctc | accgccgact | ccgtctcccg | gctgctcggc  660 |
| gaggaggccg | ggacacccga | cgtacgcggg | acggggccg  | ggcaccggat | cgtacgcgag  720 |
| gaggccgggc | ggatcctgag | ggtgaccggc | ggcaatccgc | tgctgtccca | ggcgctggtc  780 |
| gacgaacggg | cccaccgcgg | gacggacagc | gccccgata  | ccggagcgag | ggccggcgac  840 |
| accttcgaga | gggccgtgct | cgactgcctc | tatcgccacg | agccgggcgt | tcgcctggtg  900 |
| gcccaggcgc | tcgccgcgct | ggaccgcccg | gcctcaccgg | agctgctcgg | tcaactgctc  960 |
| gacgtgctgc | ccgactccac | cgtgcccgcc | gtccgcgtcc | tcgagggcgc | ggggctcgtc 1020 |
| cacgcgggcc | ggctgcgcca | tccacggatc | gtgctcgcgg | tgcgttccga | catgccggcc 1080 |
| gaggaacggc | ggcggctgca | ccagcgggcg | gccgaggtgt | tgcacgagaa | cggtgcggaa 1140 |
| gcgagcgtgg | tcgccgagca | tctggtggcc | tcggcgtgga | cggacggtgc | ctgggtggtg 1200 |
| cccgtcctcc | gggacgccgc | ggcgcacgcg | ctgtccaccg | gccgcccga  | ccacgccgcc 1260 |
| gcgtgtctgc | gcctgggcgg | tcgagccgag | accgacaagg | accggcgcaa | ctctctgatg 1320 |
| gcgatgctga | tcaccgcccg | gtggcaggtg | aatccgctgg | ccgtgaccgg | tcaggtgagt 1380 |
| cagttggtgg | aggcggcgcg | ggccgacgag | tcgtcccctt | ccacggccgt | gtccgcggtg 1440 |
| ccgtacctgt | tgtggcaggg | acgggcggag | gaggcggcca | aggcgatcag | cggttgtggt 1500 |
| gcgggcgacc | acggcccgc  | gtcgaacgag | ctgcggctga | cccgcctgct | gatcgcgctg 1560 |
| tcccatccgg | actacctggg | gacggtacgg | gaggacccga | gctcctggac | gcgggcggcg 1620 |
| acggcaccgg | actccgccag | tccgctgctg | caggccgtgt | cggtgctcgg | caacgcgctg 1680 |
| atgccgaccg | gcggggtgga | caccgtgcc  | gccgcggagc | agctgctgga | gcggcatcat 1740 |
| acggacagtg | gctccctggg | tctgttgacc | gcccccctcc | tggcgttgct | ctgtgccggc 1800 |
| cccgccgacc | gggtcgcggt | ctggggcgaa | cggctgctgg | cacgacaggg | tgtccagcac 1860 |
| acaccggcct | ggcggggtgt | catacgggcg | atccacgcgg | aagcgacgct | gcggctggga 1920 |

-continued

```
gacatggacg cggcggagcg gggcgcgcgg ttggcgctgg aggatctgcc cgcgcctgcg   1980
tggggcgtgg ccgtcggtgg tccctgggc acctgatca cctgcacgac cgagagtggc    2040
cggctgttcg aggccgaacg ctggctgtcg cagccggtac cggccggcgt cttccgcact   2100
ccggtgggcg cccactatct gatcgcccgg ggccggcacc atctggccat gggacagcac   2160
caggcggccg cggccgatct gcaccgcagc ggtgagttgg tccgttcctg ggcatcgac    2220 gtggccggac tggttccgtg cgcctggag ctggcccggg tacagctcag cctcggccac    2280
agaacgcacg ccgcgcaact gctgcaggag cagctgcagg tgtcccgcgg gctggacgac   2340
cgtactcgcg ggcgggcgct gcggctgctg gcttccacgg ccacgccggt tctgcggcgc   2400
aagctgctgt ccaaggcggt gaccgtgttg caggcatgca gtgaccagca ggagctggcc   2460
cgggccctgt ccgacacgag tcagacgctc ccacagaccg tgacgcccc acgggcccgg    2520 ctgttcgtac gtcgcgccgg ccggctggca caggcctcgg gccgggctcc agcgctgccg   2580
cagcaggtgc agcgacggtc cgcgcccagc gacgcggcgc cgacgggggg ttcctcctcg   2640
gatgcgtctt cggacggctt cgagtcccgg gatcaggacg tctgctgag cgaggccgag    2700 cgaagggtcg cggtactggc ggcacgggggg cgtaccaacc ggcagatctc caacgagctc   2760
tacatcacgg tgagtacggg ggagcagcac ctcacccggg tgtaccggaa gctggacgtc   2820
aagagccgca cggacctgcc gaaccggctc atgcccttg ccgagccgat ggcctag       2877
```

<210> SEQ ID NO 3
<211> LENGTH: 24
<212> TYPE: DNA
<213> ORGANISM: Artificial sequence
<220> FEATURE:
<223> OTHER INFORMATION: Oligonucleotides derived from S. ambofaciens DNA

<400> SEQUENCE: 3
aggtctagag tcagccgagg aaac                                            24

<210> SEQ ID NO 4
<211> LENGTH: 25
<212> TYPE: DNA
<213> ORGANISM: Artificial sequence
<220> FEATURE:
<223> OTHER INFORMATION: Oligonucleotides derived from S. ambofaciens DNA

<400> SEQUENCE: 4
catatgacga acgtgtcacg cgcgc                                           25

<210> SEQ ID NO 5
<211> LENGTH: 25
<212> TYPE: DNA
<213> ORGANISM: Artificial sequence
<220> FEATURE:
<223> OTHER INFORMATION: Oligonucleotides derived from S. ambofaciens DNA

<400> SEQUENCE: 5
catatgctgg tccatcgaga cgaac                                           25

<210> SEQ ID NO 6
<211> LENGTH: 25
<212> TYPE: DNA
<213> ORGANISM: Artificial sequence
<220> FEATURE:
<223> OTHER INFORMATION: Oligonucleotides derived from S. ambofaciens DNA -continued

<210> SEQ ID NO 6

<400> SEQUENCE: 6
tctagactct gctctctcca aggct                                      25

<210> SEQ ID NO 7
<211> LENGTH: 17
<212> TYPE: DNA
<213> ORGANISM: Artificial sequence
<220> FEATURE:
<223> OTHER INFORMATION: Oligonucleotides derived from S. ambofaciens
      DNA

<400> SEQUENCE: 7
cgcggcatgc tcttcct                                               17

<210> SEQ ID NO 8
<211> LENGTH: 20
<212> TYPE: DNA
<213> ORGANISM: Artificial sequence
<220> FEATURE:
<223> OTHER INFORMATION: Oligonucleotides derived from S. ambofaciens
      DNA

<400> SEQUENCE: 8
aggtggcgta cgtggagaac                                            20

<210> SEQ ID NO 9
<211> LENGTH: 20
<212> TYPE: DNA
<213> ORGANISM: Artificial sequence
<220> FEATURE:
<223> OTHER INFORMATION: Oligonucleotides derived from S. ambofaciens
      DNA

<400> SEQUENCE: 9
gtcgccggat caccgaggaa                                            20

<210> SEQ ID NO 10
<211> LENGTH: 20
<212> TYPE: DNA
<213> ORGANISM: Artificial sequence
<220> FEATURE:
<223> OTHER INFORMATION: Oligonucleotides derived from S. ambofaciens
      DNA

<400> SEQUENCE: 10
aggtcgcgga acgccttgtc                                            20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotides derived from S. ambofaciens
      DNA

<400> SEQUENCE: 11
tgcctgcggt gctccaccaa                                            20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotides derived from S. ambofaciens
      DNA

<400> SEQUENCE: 12
cgtcgtcttc tcctccatcg                                            20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotides derived from S. ambofaciens
      DNA

<400> SEQUENCE: 13
accgcgccgg aggtgagaca                                            20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotides derived from S. ambofaciens
      DNA

<400> SEQUENCE: 14
gctgctcgcc tgcgtggaca                                            20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotides derived from S. ambofaciens
      DNA

<400> SEQUENCE: 15
ggaacagctc gccgtactcc                                            20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotides derived from S. ambofaciens
      DNA

<400> SEQUENCE: 16
ccgaactcgt cggcgtatgg                                            20

<210> SEQ ID NO 17
<211> LENGTH: 20
<212> TYPE: DNA
<213> ORGANISM: Artificial sequence
<220> FEATURE:
<223> OTHER INFORMATION: Oligonucleotides derived from S. ambofaciens
      DNA

<400> SEQUENCE: 17
ctggagacct tcggggagtg                                            20

<210> SEQ ID NO 18
<211> LENGTH: 20
<212> TYPE: DNA

```
<213> ORGANISM: Artificial sequence
<220> FEATURE:
<223> OTHER INFORMATION: Oligonucleotides derived from S. ambofaciens
      DNA

<400> SEQUENCE: 18
tgcccgagca ctccgaaatg                                              20
```